United States Patent [19]

Sugimura et al.

[11] Patent Number: 5,102,997

[45] Date of Patent: * Apr. 7, 1992

[54] 2-(1-ACETIMIDOYL-5-CARBAMOYLPYR-ROLIDIN-3-YLTHIO-6-(1-HYDROXYE-THYL)-1-METHYLCARBAPEN-2-EM-3-CARBOXYLIC ACID

[75] Inventors: Yukio Sugimura; Toshihiko Hashimoto; Teruo Tanaka; Kimio Iino; Tomoyuki Shibata; Masayuki Iwata, all of Hiromachi, Japan

[73] Assignee: Sankyo Company Limited, Tokyo, Japan

[ * ] Notice: The portion of the term of this patent subsequent to Apr. 26, 2005 has been disclaimed.

[21] Appl. No.: 463,773

[22] Filed: Jan. 5, 1990

Related U.S. Application Data

[63] Continuation of Ser. No. 296,279, Jan. 11, 1989, abandoned, which is a continuation of Ser. No. 185,318, Apr. 20, 1988, abandoned, which is a continuation of Ser. No. 87,994, Aug. 17, 1987, abandoned, which is a continuation of Ser. No. 714,373, Mar. 21, 1985, abandoned.

[30] Foreign Application Priority Data

Mar. 27, 1984 [JP] Japan .................. 59-59279

[51] Int. Cl.⁵ .................. C07D 487/04; A61L 31/40
[52] U.S. Cl. .................. 540/350; 514/210
[58] Field of Search .................. 540/350, 310; 514/210

[56] References Cited

U.S. PATENT DOCUMENTS

| | | | |
|---|---|---|---|
| 1,696,923 | 9/1927 | Christensen et al. ............... | 540/350 |
| 4,206,219 | 6/1980 | Christensen et al. . | |
| 4,260,627 | 4/1981 | Christensen et al. . | |
| 4,312,871 | 1/1982 | Christensen et al. . | |
| 4,650,794 | 3/1987 | Christensen et al. ............... | 540/310 |
| 4,740,507 | 4/1988 | Sugumura et al. ................. | 540/350 |
| 4,943,569 | 7/1990 | Sunagawa et al. ................. | 540/350 |
| 4,962,103 | 10/1990 | Sunagawa et al. ................. | 514/210 |

FOREIGN PATENT DOCUMENTS

| | | |
|---|---|---|
| 010317 | 4/1980 | European Pat. Off. . |
| 060077 | 9/1982 | European Pat. Off. . |
| 071908 | 2/1983 | European Pat. Off. . |
| 089139 | 9/1983 | European Pat. Off. . |
| 126587 | 11/1984 | European Pat. Off. . |

Primary Examiner—Nicholas S. Rizzo
Attorney, Agent, or Firm—Frishauf, Holtz, Goodman & Woodward

[57] ABSTRACT

Compounds of formula (I):

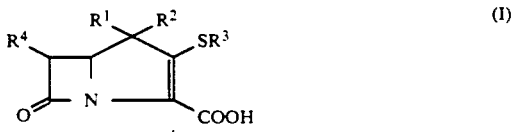

wherein:
one or both of $R^1$ and $R^2$ are selected from a variety of organic groups;
$R^3$ is an optionally substituted heterocycle; and
$R^4$ is hydrogen or optionally substituted alkyl or alkoxy.

and salts and esters thereof have valuable antibiotic activity.

2 Claims, No Drawings

2-(1-ACETIMIDOYL-5-CARBAMOYLPYRROLIDIN-3-YLTHIO-6-(1-HYDROXYETHYL)-1-METHYLCARBAPEN-2-EM-3-CARBOXYLIC ACID

This application is a continuation of application Ser. No. 07/296,279, filed Jan. 11, 1989 now abandoned; which is a continuation of Ser. No. 07/185,318 filed Apr. 20, 1988 (abandoned); which is a continuation of Ser. No. 07/087,994 filed Aug. 17, 1987 (abandoned); which is a continuation of Ser. No. 06/714,373 filed Mar. 21, 1985 (abandoned).

The present invention relates to a series of new carbapenem compounds and to compositions containing the compounds, and provides a process for preparing these compounds.

The penicillins form a well known class of antibiotics, which have found considerable use in human and animal therapy for many years. Chemically, the penicillins have in common a β-lactam structure, commonly referred to as "penam", which may be represented by the following formula:

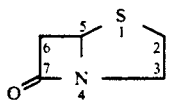

However, although the penicillins still form a valuable weapon in the pharmaceutical armory, the development of new, and often penicillin-resistant, strains of pathogenic bacteria has increasingly made it necessary to search for new types of antibiotic.

In recent years, great interest has been shown in compounds having a carbapenem structure, that is compounds having a carbon atom in place of the sulfur atom at the 1-position and having a double bond between the carbon atoms in the 2- and 3-positions of the basic penam structure. The carbapenem structure may be represented by the following formula

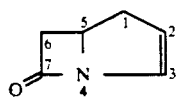

These penam and carbapenem structures form the basis for the semi-systematic nomenclature of the penicillin derivatives in accordance with the recommendations of the International Union of Pure and Applied Chemistry (IUPAC), and this nomenclature is generally accepted by those skilled in the art throughout the world and is used herein. The numbering system employed herein is that illustrated on the above formulae.

Of the known carbapenem derivatives, the best known is a compound called "thienamycin", whose semi-systematic name is 2-(2-aminoethylthio)-6-(1-hydroxyethyl)carbapen-2-em-3-carboxylic acid. Although thienamycin is known to have remarkably potent and broad antibacterial activity, its chemical stability in the human body is poor, which restricts its practical use. Various attempts have, therefore, been made to modify the chemical structure of thienamycin in order to improve its chemical stability whilst maintaining or improving its superior activity.

In recent years, as interest in the carbapenem compounds has increased, a large number of carbapenem derivatives has been proposed in a variety of publications in an attempt to overcome various of the problems associated with thienamycin, and, in particular, in order to improve stability and improve antibacterial activity. Of the prior art, the closest prior art to the present invention is believed to be European Patent Publication No. 10,317, which discloses a series of carbapenem compounds in which substituents at the 1-, 2- and 6-positions are chosen from an extremely long list of groups and atoms, whose general terms cover some of the appropriate substituents on the compounds of the invention. Also U.S. Pat. 4,552,873 which issued on application Ser. No. 407,914, filed 13th Aug. 1982 is close prior art. It discloses a limited class of carbapenem derivatives having a heterocyclyl-thio group at the 2-position; the compounds of this prior art, however, differ from those of the present invention in that they lack a substituent at the 1-position. Also relevant prior art, in that they disclose compounds having substituents at the 1-position, are U.S. Pat. Nos. 4,206,219 and No. 4,260,627; the compounds disclosed in these U.S. patents, however, differ from those of the present invention in that, respectively, they lack a substituent at the 2-position or, whilst having a wide range of substituents at the 2-position, do not contemplate a heterocyclyl-thio substituent.

We have now discovered a class of compounds, of which those compounds investigated have been found to exhibit far better absorption and metabolic stability (as evidenced by improved recovery rates in the urine) than the compounds of U.S. Pat. No. 4,552,873 and which have a broader antibacterial spectrum, stronger activity and greater stability than thienamycin.

BRIEF SUMMARY OF INVENTION

The compounds of the invention are those compounds which may be represented by the formula (I):

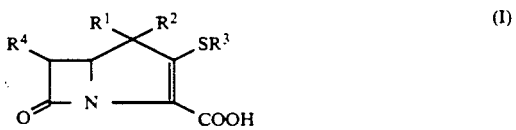

wherein:

$R^1$ and $R^2$ are independently selected from the group consisting of hydrogen, provided that $R^1$ and $R^2$ are not both hydrogen, halogen atoms, $C_2-C_7$ alkoxycarbonyl groups and substituted and unsubstituted $C_1-C_{10}$ alkyl, $C_2-C_6$ alkenyl, $C_2-C_6$ alkynyl, $C_1-C_6$ alkoxy, $C_1-C_6$ alkylthio, $C_3-C_8$ cycloalkyl, $C_6-C_{10}$ carbocyclic aryl, aralkyl, aralkenyl and aralkynyl groups wherein, in said aralkyl, aralkenyl and aralkynyl groups, the aryl part is a $C_6-C_{10}$ carbocyclic aryl group and the alkyl, alkenyl or alkynyl part contains up to 6 carbon atoms, and wherein the substituents on said alkyl, alkenyl, alkynyl, alkoxy, alkylthio, cycloalkyl, aryl, aralkyl, aralkenyl and aralkynyl groups are selected from the group consisting of:

(a) halogen atoms, $C_1-C_6$ alkyl or haloalkyl groups but only on said aryl groups or the aryl part of said aralkyl, aralkenyl or aralkynyl groups, $C_1-C_6$ alkoxy groups, $C_1-C_6$ alkylthio groups, hydroxy groups and phenyl groups, or $R^1$ and $R^2$, together with the carbon atom to which they are attached, form a $C_3-C_8$ alicyclic ring;

$R^3$ represents a heterocyclic ring having from 4 to 8 ring atoms, of which from 1 to 3 ring atoms are selected from the group consisting of oxygen, sulfur and nitrogen atoms, which heterocyclic ring is unsubstituted or has from 1 to 3 substituents selected from the group consisting of:

(b) oxo groups, $C_1$–$C_6$ alkyl groups, alkoxyalkyl groups where the alkyl part and the alkoxy part both have from 1 to 6 carbon atoms, cyanoalkyl groups where the alkyl part has from 1 to 6 carbon atoms, $C_1$–$C_6$ haloalkyl groups, $C_1$–$C_6$ alkoxy groups, hydroxy groups, amino groups, halogen atoms, $C_1$–$C_7$ aliphatic acyloxy groups, $C_1$–$C_7$ aliphatic acylamino groups, cyano groups, azido groups, carboxy groups, $C_2$–$C_7$ alkoxycarbonyl groups, carbamoyl groups, thiocarbamoyl groups, $C_1$–$C_6$ alkylthio groups, $C_1$–$C_6$ alkylsulfinyl groups, $C_1$–$C_6$ alkylsulfonyl groups, nitro groups, $C_2$–$C_6$ alkenyl groups, cycloalkylalkyl groups where the cycloalkyl part has from 3 to 8 carbon atoms and the alkyl part has from 1 to 6 carbon atoms, $C_6$–$C_{10}$ carbocyclic aryl groups, $C_1$–$C_7$ aliphatic acyl groups, $C_4$–$C_9$ cycloalkanecarbonyl groups, cycloalkylalkanoyl groups where the cycloalkyl part has from 3 to 8 carbon atoms and the alkanoyl part has from 2 to 7 carbon atoms, aromatic carbocyclic acyl groups, araliphatic acyl groups where the aryl part is $C_6$–$C_{10}$ carbocyclic aryl and the aliphatic acyl part is $C_2$–$C_7$, heterocyclic acyl groups, heterocyclic-substituted $C_2$–$C_7$ aliphatic acyl groups, aromatic acyl-substituted $C_1$–$C_6$ alkyl groups, sulfo groups, $C_1$–$C_6$ alkoxysulfonyl groups, $C_1$–$C_6$ alkenylsulfonyl groups, $C_1$–$C_6$ alkynylsulfonyl groups, $C_3$–$C_8$ cycloalkylsulfonyl groups, cycloalkylalkylsulfonyl groups where the cycloalkyl part has from 3 to 8 carbon atoms and the alkyl part has from 1 to 6 carbon atoms, $C_6$–$C_{10}$ carbocyclic arylsulfonyl groups, aralkylsulfonyl groups where the aryl part is $C_6$–$C_{10}$ carbocyclic aryl and the alkyl part is $C_1$–$C_6$ alkyl, heterocyclyl-sulfonyl groups, heterocyclic-substituted $C_1$–$C_6$ alkylsulfonyl groups, aliphatic, carbocyclic aromatic and heterocyclic acyl imidoyl groups of formula —C($R^5$)=N—$R^6$, wherein:

$R^5$ and $R^6$ are the same or different and each represents hydrogen, a $C_1$–$C_6$ alkyl group, a $C_1$–$C_6$ alkyl group having from 1 to 3 substituents selected from the group consisting of $C_1$–$C_6$ alkoxy, cyano, phenyl and halogen substituents, a phenyl group or an aromatic heterocyclic group,
alkylcarbamoyl, alkylthiocarbamoyl, dialkylcarbamoyl and dialkylthiocarbamoyl groups where each alkyl part has from 1 to 6 carbon atoms, amidino groups, mono-, di- and tri-($C_1$–$C_6$ alkyl)amidino groups, aralkoxycarbonyl groups where the aryl part is $C_6$–$C_{10}$ carbocyclic aryl and the alkoxy part is $C_1$–$C_6$ alkoxy, aliphatic acyl groups having at least one amino substituent, aliphatic acyloxyalkyl groups where the acyl part is $C_1$–$C_7$ and the alkyl part is $C_1$–$C_6$, aralkyl groups where the aryl part is $C_6$–$C_{10}$ carbocyclic aryl and the alkyl part is $C_1$–$C_6$ alkyl, $C_1$–$C_6$ hydroxyalkyl groups, arylcarbamoyl and aryl(thiocarbamoyl) groups where the aryl part is $C_6$–$C_{10}$ carbocyclic aryl, cycloalkylcarbamoyl and cycloalkyl(thiocarbamoyl) groups where the cycloalkyl part is $C_3$–$C_8$ cycloalkyl, and alkoxycarbonylalkyl groups where the alkoxy and alkyl parts are both $C_1$–$C_6$.

$R^4$ represents a hydrogen atom or a $C_1$–$C_6$ alkyl or alkoxy group which is unsubstituted or has from 1 to 3 substituents selected from the group consisting of:

(c) hydroxy groups, aryloxycarbonyloxy groups where the aryl part is $C_6$–$C_{10}$ carbocyclic aryl and is unsubstituted or substituted, alkenyloxycarbonyloxy groups where the alkenyl part is $C_2$–$C_6$ and is unsubstituted or substituted, alkoxycarbonyloxy groups where the alkoxy part is $C_1$–$C_6$ and is unsubstituted or substituted, trialkylsilyloxy groups where each alkyl is $C_1$–$C_6$, $C_1$–$C_6$ alkoxy groups, $C_1$–$C_7$ aliphatic acyloxy groups, $C_1$–$C_6$ alkylsulfonyloxy groups, arylsulfonyloxy groups where the aryl part is $C_6$–$C_{10}$ carbocyclic aryl and is unsubstituted or substituted, mercapto groups, $C_1$–$C_6$ alkylthio groups, amino groups and $C_1$–$C_7$ aliphatic acylamino groups, the substituents on said aryl, alkenyl and alkoxy parts being as defined in (a) above;

and pharmaceutically acceptable salts and esters thereof.

The invention also provides a pharmaceutical composition comprising an effective amount of an antibacterial agent in admixture with a pharmaceutically acceptable carrier or diluent, wherein the antibacterial agent is selected from the group consisting of compounds of formula (I) and pharmaceutically acceptable salts and esters thereof.

DETAILED DESCRIPTION OF INVENTION

In the compounds of the invention, one of $R^1$ and $R^2$, but not both, may be hydrogen and the other may be selected from the groups and atoms defined below, or both may be selected from these groups and atoms.

$R^1$ and $R^2$ may represent alkyl groups having from 1 to 10 carbon atoms, for example the methyl, ethyl, propyl, isopropyl, butyl, isobutyl, sec-butyl, t-butyl, pentyl, isopentyl, neopentyl, t-pentyl, 2-methylbutyl, hexyl, isohexyl, 2-methylpentyl, heptyl, octyl, 2-ethylhexyl, nonyl or decyl groups, preferably the $C_1$–$C_3$ alkyl groups (i.e. the methyl, ethyl, propyl and isopropyl groups) and more preferably the methyl group.

$R^1$ or $R^2$ may also represent alkenyl groups having from 2 to 6 carbon atoms, for example the vinyl, allyl, methallyl, 1-propenyl, 1-butenyl, 2-butenyl, 3-butenyl, pentenyl (1,2,3 or 4) or hexenyl (1,2,3,4 or 5) groups, preferably a $C_2$ or $C_3$ alkenyl group and more preferably a vinyl or allyl group.

$R^1$ and $R^2$ may also represent alkynyl groups having from 2 to 6 carbon atoms, for example the ethynyl, propargyl, 1-propynyl, 1-butynyl, 2-butynyl 3-butynyl, pentynyl (1,2,3 or 4) or hexynyl (1,2,3,4 or 5) groups. Of these, we prefer $C_2$ and $C_3$ alkynyl groups, particularly the ethynyl and propargyl groups.

Where $R^1$ or $R^2$ represents an alkoxy group, this has from 1 to 6 carbon atoms and may be a straight or branched chain group. Examples include the methoxy, ethoxy, propoxy, isopropoxy, butoxy, isobutoxy, sec-butoxy, t-butoxy, pentyloxy, isopentyloxy, neopentyloxy, t-pentyloxy, hexyloxy and isohexyloxy groups, of which the $C_1$–$C_3$ alkoxy groups (methoxy, ethoxy, propoxy and isopropoxy) are preferred.

Where $R^1$ or $R^2$ represents an alkylthio group, this has from 1 to 6 carbon atoms and may be a straight or branched chain group. Examples include the methylthio, ethylthio, propylthio, isopropylthio, butylthio, isobutylthio, sec-burylthio, t-butylthio, pentylthio, isopentylthio, neopentylthio, t-pentylthio, hexylthio and isohexylthio groups, of which the $C_1$–$C_3$ alkylthio groups (i.e. methylthio, ethylthio, propylthio and isopropylthio) are preferred.

Where $R^1$ or $R^2$ represents a cycloalkyl group, this has from 3 to 8 carbon atoms and examples include the cyclopropyl, cyclobutyl, cyclopentyl, cyclohexyl, cycloheptyl and cyclooctyl groups, particularly the $C_3$-$C_6$ cycloalkyl groups (cyclopropyl, cyclobutyl, cyclopentyl and cyclohexyl).

Where $R^1$ or $R^2$ represents an aryl group, this is a carbocyclic aromatic group, which may have from 6 to 10 carbon atoms, for example a phenyl, 1-naphthyl or 2-naphthyl group, preferably a phenyl group.

Where $R^1$ or $R^2$ represents an aralkyl, aralkenyl or aralkynyl group, the aryl part of this group is as defined above where $R^1$ or $R^2$ is itself an aryl group and is preferably a phenyl group, and the alkyl, alkenyl or alkynyl part is as defined above where $R^1$ or $R^2$ is itself an alkyl, alkenyl or alkynyl group, and is preferably a methyl, ethyl, vinyl, allyl, ethynyl or propargyl group, more preferably a methyl group.

Alternatively, $R^1$ and $R^2$, together with the carbon atom to which they are attached, may represent an alicyclic ring system having from 3 to 8, preferably from 3 to 6, carbon atoms and more preferably $R^1$ and $R^2$ together represent an ethylene, trimethylene, tetramethylene or pentamethylene group.

Where $R^1$ or $R^2$ represents an alkyl, alkenyl, alkynyl, alkoxy, alkylthio, cycloalkyl, aryl, aralkyl, aralkenyl, or aralkynyl group, they may be unsubstituted or they may be substituted. If substituted, they have from 1 to 3 substituents, which are selected from the group consisting of the following:

halogen atoms, for example fluorine, chlorine, bromine or iodine atoms, particularly fluorine, chlorine or bromine atoms; where there are 2 or 3 halogen substituents, these may be all on the same carbon atom or they may be on different carbon atoms, preferably on the same carbon atom;

hydroxy, mercapto, nitro, cyano and amino groups;

alkoxy groups, preferably having from 1 to 3 carbon atoms and more preferably being the methoxy or ethoxy groups;

alkylthio groups, preferably having from 1 to 3 carbon atoms and more preferably being the methylthio or ethylthio groups;

carbocyclic aryl groups, for example as exemplified above in relation to $R^1$ and $R^2$, particularly the phenyl group;

except where the substituent is on an alkyl, alkenyl, alkynyl, alkoxy or alkylthio group, an alkyl group preferably having from 1 to 3 carbon atoms and more preferably being the methyl or ethyl group; and except where the substituent is on an alkyl, alkenyl, alkynyl, alkoxy or alkylthio group, a haloalkyl group having from 1 to 6, preferably 1 to 3, more preferably 1 or 2 and most preferably 1, carbon atoms and from 1 to 3 halogen, e.g. fluorine, chlorine, bromine or iodine, atoms; examples include the fluoromethyl, chloromethyl, bromomethyl, iodomethyl, trifluoromethyl, trichloromethyl, 2,2,2-trichloroethyl and 2,2,2-trifluoroethyl groups.

$R^3$ represents a heterocyclic group having from 4 to 8 ring atoms, of which from 1 to 3 are hetero-atoms selected from the group consisting of nitrogen, oxygen and sulfur atoms, the remainder being carbon atoms. The heterocyclic ring may be saturated or partially saturated. In the heterocyclic groups represented by $R^3$, the atom through which the heterocyclic group is attached to the sulfur atom of $-SR^3$ is preferably a carbon atom. Examples of such heterocyclic ring systems which may be represented by $R^3$ include the 2-azetidinyl, 3-azetidinyl, 2-pyrrolidinyl, 3-pyrrolidinyl, 2-piperidyl, 3-piperidyl, 4-piperidyl, hexahydro-1H-azepin-4-yl, octahydroazocin-5-yl, oxazolidin-5-yl, thiazolidin-5-yl, 2-morpholinyl, 1,4-thiazin-2-yl, hexahydropyrimidin-5-yl, hexahydropyridazin-4-yl, perhydroazocin-3-yl, perhydroazepin-3-yl and 3, 4, 5, 6-tetrahydropyrimidin-5-yl These heterocyclic ring systems may be substituted or unsubstituted and a wide range of substituents are possible on the carbon, nitrogen and possibly sulfur atoms of the heterocyclic ring. The nature of permissible substituents will, of course, depend upon the atom of the heterocyclic ring to which they are attached.

Examples of substituents which may be attached to ring carbon atoms include:

$C_1$-$C_6$ alkyl groups, which may be straight or branched chain groups, particularly the methyl, ethyl, propyl, isopropyl, butyl, isobutyl, sec-butyl, t-butyl, pentyl and isopentyl groups;

alkoxyalkyl groups where both the alkoxy and the alkyl parts have from 1 to 6 carbon atoms, for example the methoxymethyl, ethoxymethyl, propoxymethyl, isopropoxymethyl, butoxymethyl, 2-methoxyethyl, 1-methoxyethyl, 3-methoxypropyl, 2-methoxypropyl and 4-ethoxybutyl groups;

cyanoalkyl groups where the alkyl part is $C_1$-$C_6$ alkyl, such as the cyanomethyl, 2-cyanoethyl, 1-cyanoethyl, 3-cyanopropyl, 2-cyanopropyl and 4-cyanobutyl groups;

$C_1$-$C_6$ haloalkyl groups (preferably having 1, 2 or 3 halogen atoms, such as the chlorine, fluorine, bromine or iodine atoms), for example the trifluoromethyl, 2-fluoroethyl, 2,2,2-trifluoroethyl, 2,2,2-trichloroethyl, 2 chloroethyl, 2-bromoethyl, 3-fluoropropyl, 2-fluoropropyl, 4-chlorobutyl and 3-fluorobutyl groups;

$C_1$-$C_6$ alkoxy groups, which may be straight or branched chain groups, for example the methoxy, ethoxy, propoxy, isopropoxy, butoxy, isobutoxy, sec-butoxy and t-butoxy groups halogen atoms, such as the fluorine, chlorine, bromine and iodine atoms;

$C_1$-$C_7$, preferably $C_2$ to $C_5$, aliphatic acyloxy groups, such as the acetoxy, propionyloxy, butyryloxy and isobutyryloxy groups;

$C_1$-$C_7$, preferably $C_2$ to $C_5$, aliphatic acylamino groups, such as the acetamido, propionamido, butyramido and isobutyramido groups;

the hydroxy, amino, cyano, nitro, azido, carbamoyl and carboxy groups;

alkoxycarbonyl groups where the alkoxy part is $C_1$-$C_6$ alkoxy, such as the methoxycarbonyl, ethoxycarbonyl, propoxycarbonyl, isopropoxycarbonyl, butoxycarbonyl, isobutoxycarbonyl, sec-butoxycarbonyl and t-butoxycarbonyl groups;

$C_1$-$C_6$ alkylthio groups, which may be straight or branched chain groups, such as the methylthio, ethylthio, propylthio, isopropylthio, butylthio and isobutylthio groups;

$C_1$-$C_6$ alkylsulfinyl groups, which may be straight or branched chain groups, such as the methylsulfinyl, ethylsulfinyl, propylsulfinyl, isopropylsulfinyl, butylsulfinyl and isobutylsulfinyl groups;

$C_1$-$C_6$ alkylsulfonyl groups, which may be straight or branched chain groups, such as the methylsulfonyl, ethylsulfonyl, propylsulfonyl, isopropylsulfonyl, butylsulfonyl and isobutylsulfonyl groups; and the oxo group (i.e. a doubly bonded oxygen atom, forming, with the carbon atom to which it is attached, a carbonyl group).

Examples of substituents which may be attached to ring nitrogen atoms include the following:

$C_1$–$C_6$ alkyl groups, which may be straight or branched chain groups, such as the methyl, ethyl, propyl, isopropyl, butyl, isobutyl, sec-butyl, t-butyl, pentyl and isopentyl groups; these alkyl groups may be unsubstituted or may have one or more substituents selected from the group consisting of those substituents listed above as possible substituents on ring carbon atoms, particularly hydroxy groups and halogen (especially fluorine) atoms; $C_2$–$C_6$ alkenyl groups, which may be straight or branched chain groups, such as the vinyl, allyl, 1-propenyl, isopropenyl, 2-butenyl and 2-pentenyl groups;

$C_2$–$C_6$ alkynyl groups, such as the ethynyl, 1-propynyl, propargyl, 2-butynyl and 4-pentynyl groups;

$C_3$–$C_8$ cycloalkyl groups, such as the cyclopropyl, cyclobutyl, cyclopentyl, cyclohexyl and cycloheptyl groups;

cycloalkylalkyl groups, in which the cycloalkyl part is $C_3$–$C_8$ cycloalkyl and the alkyl part (which may be straight or branched chain) is $C_1$–$C_6$ alkyl, such as the cyclopropylmethyl, cyclobutylmethyl, cyclopentylmethyl, cyclohexylmethyl, cycloheptylmethyl, 2-cyclopentylethyl, 2-cyclohexylethyl, 3-cyclopentylpropyl, 2-cyclopentylpropyl, 3-cyclohexylpropyl, 2-cyclohexylpropyl, 4-cyclopentylbutyl and 3-cyclohexylbutyl groups;

carbocyclic aryl groups, preferably having from 6 to 10 ring carbon atoms, such as the phenyl, 1-naphthyl and 2-naphthyl groups;

aralkyl groups, of which the alkyl part preferably has from 1 to 6, more preferably from 1 to 3, carbon atoms and the aryl part is a carbocyclic aryl group preferably having from 6 to 10 ring carbon atoms, for example the benzyl, phenethyl and 3-phenylpropyl groups;

$C_1$–$C_7$ aliphatic acyl groups, of which the aliphatic part may be saturated or have carbon-carbon unsaturation, such as the formyl, acetyl, propionyl, butyryl, isobutyryl, acryloyl, methacryloyl, crotonoyl, propioloyl and methylpropioloyl groups, and may be unsubstituted or may have one or more substituents selected from the group consisting of those substituents listed above as possible substituents on ring carbon atoms, particularly amino groups;

cycloalkanecarbonyl groups, where the cycloalkane part is $C_3$–$C_8$ cycloalkane, such as the cyclopropanecarbonyl, cyclobutanecarbonyl, cyclopentanecarbonyl and cyclohexanecarbonyl groups;

cycloalkylalkanoyl groups, where the cycloalkane part is $C_3$–$C_8$ cycloalkane and the alkanoyl part is $C_2$–$C_7$ alkanoyl, such as the cyclopropylacetyl, cyclobutylacetyl, cyclopentylacetyl, cyclohexylacetyl, 3-cyclopentylpropionyl, 3-cyclohexylpropionyl, 4-cyclopentylbutyryl and 4-cyclohexylbutyryl groups;

aromatic carbocyclic carboxylic acyl groups, wherein the aryl part preferably has from 6 to 10 ring carbon atoms, such as the benzoyl, 1-naphthoyl and 2-naphthoyl groups;

carbocyclic aromatic-substituted aliphatic carboxylic acyl groups wherein the aromatic part preferably has from 6 to 10 ring carbon atoms and the aliphatic acyl part preferably has from 2 to 7 carbon atoms and may be saturated or unsaturated, for example the phenylacetyl, 1-naphthylacetyl, 3-phenylpropionyl, hydratropoyl, cinnamoyl and phenylpropioloyl groups;

heterocyclic carboxylic acyl groups, such as the furoyl, thenoyl, nicotinoyl, isonicotinoyl, 4-thiazolecarbonyl, 5-pyrimidinecarbonyl, 2-pyridinecarbonyl, 1-aziridinecarbonyl, 1-azetidinecarbonyl, 3-azetidinecarbonyl, 1-pyrrolidinecarbonyl, 2-pyrrolidinecarbonyl, 3-pyrrolidinecarbonyl, 1-piperidinecarbonyl, 2-piperidinecarbonyl, 4-piperidinecarbonyl and 1-morpholinecarbonyl groups;

heterocyclic-substituted aliphatic acyl groups, wherein the aliphatic acyl part preferably has from 2 to 7, and more preferably from 2 to 4 carbon atoms, and the heterocyclic part, which may be saturated, unsaturated or partially saturated, preferably has from 3 to 8 ring atoms of which from 1 to 3 are hetero-atoms selected from the group consisting of oxygen, sulfur and nitrogen atoms, such as the 2-thienylacetyl, 3-(2-thienyl)propionyl, 4-thiazolylacetyl, 2-pyridylacetyl, 4-pyridylacetyl, 5-pyrimidylacetyl, 1-aziridinylacetyl, 1-azetidinylacetyl, 3-azetidinylacetyl, 1-pyrrolidinylacetyl, 2-pyrrolidinylacetyl, 3-pyrrolidinylacetyl, 3-(2-pyrrolidinyl)propionyl, piperidinoacetyl, 2-piperidylacetyl, 4-piperidylacetyl and morpholinoacetyl groups;

aromatic acyl-substituted alkyl groups, where the acyl part is an aromatic carbocyclic carboxylic acyl group and is preferably selected from those groups listed above and the alkyl part is $C_1$–$C_6$ alkyl and is preferably selected from those groups listed above, particularly methyl or ethyl, e.g. the phenacyl group;

the sulfo group;

$C_1$–$C_6$ alkoxysulfonyl groups, such as the methoxysulfonyl, ethoxysulfonyl, propoxysulfonyl and isopropoxysulfonyl groups;

$C_1$–$C_6$ alkylsulfonyl groups, which may be straight or branched chain groups, such as the methylsulfonyl, ethylsulfonyl, propylsulfonyl, isopropylsulfonyl, butylsulfonyl and isobutylsulfonyl groups;

$C_2$–$C_6$ alkenylsulfonyl groups, such as the allylsulfonyl, isopropenylsulfonyl and 2-butenylsulfonyl groups;

$C_2$–$C_6$ alkynylsulfonyl groups, such as the ethynylsulfonyl, propargylsulfonyl and 2-butynylsulfonyl groups;

$C_3$–$C_8$ cycloalkylsulfonyl groups, such as the cyclopropylsulfonyl, cyclobutylsulfonyl, cyclopentylsulfonyl and cyclohexylsulfonyl groups;

cycloalkylalkylsulfonyl groups, where the cycloalkyl part is $C_3$–$C_8$ cycloalkyl and the alkyl part (which may be straight or branched chain) is $C_1$–$C_6$ alkyl, such as the cyclopropylmethylsulfonyl, cyclobutylmethylsulfonyl, cyclopentylmethylsulfonyl, cyclohexylmethylsulfonyl, 2-cyclopentylethylsulfonyl, 2-cyclohexylethylsulfonyl, 3-cyclopentylpropylsulfonyl and 2-cyclopentylpropylsulfonyl groups;

arylsulfonyl groups, wherein the aryl part is a carbocyclic aromatic group preferably having from 6 to 10 ring carbon atoms, such as the phenylsulfonyl, 1-naphthylsulfonyl and 2-naphthylsulfonyl groups;

aralkylsulfonyl groups, in which the aryl part is a carbocyclic aromatic group preferably having from 6 to 10 ring carbon atoms and the alkyl part is a $C_1$–$C_6$ alkyl group, which may be a straight or branched chain group, for example the benzylsulfonyl, phenethylsulfonyl, 3-phenylpropylsulfonyl and 2-phenylpropylsulfonyl groups;

aromatic heterocyclic-sulfonyl groups, such as the 2-thiophenesulfonyl, 4-thiazolesulfonyl, 2-pyridinesulfonyl and 4-pyridinesulfonyl groups;

(aromatic heterocyclic)-substituted alkylsulfonyl groups, in which the alkyl part, which may be straight or branched chain, preferably has from 1 to 6, more preferably from 1 to 3, carbon atoms, for example the 2-thienylmethylsulfonyl, 3-(2-thienyl)propylsulfonyl, 4-thiazolylmethylsulfonyl, 2-pyridylmethylsulfonyl and 4-pyridylmethylsulfonyl groups;

aliphatic, substituted aliphatic, aromatic or heterocyclic acyl imidoyl groups which may be represented by the formula —$(R^5)C=N-R^6$, in which $R^5$ and $R^6$ are the same or different and each represents hydrogen, a $C_1-C_6$, preferably $C_1-C_3$, alkyl group (for example a methyl, ethyl, propyl or isopropyl group), an alkoxyalkyl group where the alkoxy and alkyl parts both have from 1 to 6, preferably 1 to 3 more preferably 1 or 2, carbon atoms (for example a methoxymethyl or ethoxymethyl group), a cyanoalkyl group where the alkyl part (which may be straight or branched chain) has from 1 to 6 carbon atoms (for example a cyanomethyl, 1-cyanoethyl or 2-cyanoethyl group), an aromatic heterocyclic group (such as a pyridyl, furyl or thienyl group), a phenyl group, a benzyl group or a $C_1-C_6$ haloalkyl group (such as a chloromethyl or fluoromethyl group), particularly the formimidoyl, acetimidoyl, N-methylformimidoyl, N-methylacetimidoyl, propionimidoyl, α-methoxyacetimidoyl, α-fluoroacetimidoyl, nicotinimidoyl and benzimidoyl groups;

carbamoyl, thiocarbamoyl and amidino groups and alkyl-substituted derivatives thereof of formula —(Z:-)C—$NR^7R^8$, in which $R^7$ and $R^8$ are the same or different and each represents hydrogen or a $C_1-C_6$, preferably $C_1-C_3$, alkyl group (such as a methyl, ethyl, propyl or isopropyl group) and Z represents an oxygen or sulfur atom, an imino group or a $C_1-C_6$ alkylimino group (such as the methylimino, ethylimino, propylimino or isopropylimino group);

alkoxycarbonyl groups, where the alkoxy part is $C_1-C_6$ alkoxy, such as the methoxycarbonyl, ethoxycarbonyl, butoxycarbonyl and isobutoxycarbonyl groups; and aralkyloxycarbonyl groups, in which the aryl part is a carbocyclic aromatic group preferably having from 6 to 10 ring carbon atoms and the alkyl part is a $C_1-C_6$, preferably $C_1-C_3$, alkyl group, for example the benzyloxycarbonyl and phenethyloxycarbonyl groups.

Where the sulfur atom of the heterocyclic ring represented by $R^3$ is substituted, the substituents are preferably 1 or 2 oxygen atoms, so as to form, with the sulfur atom, a sulfinyl or sulfonyl group.

$R^4$ represents hydrogen, or a $C_1-C_6$ alkyl or $C_1-C_6$ alkoxy group. Where $R^4$ represents an alkoxy group, this may be a straight or branched chain group and is preferably a $C_1-C_4$ alkoxy group, particularly a methoxy, ethoxy, propoxy, isopropoxy, butoxy, isobutoxy or t-butoxy group. Where $R^4$ is an alkyl group, this may be a straight or branched chain group and is preferably a $C_1-C_5$ alkyl group, for example a methyl, ethyl, propyl, isopropyl, butyl, isobutyl, t-butyl, pentyl or isopentyl group. These alkyl and alkoxy groups may be unsubstituted or may have one or more, preferably from 1 to 3, substituents which may be selected from the group consisting of the following: hydroxy groups (which may, if desired, be protected by any conventional protecting group, for example a benzyloxycarbonyl, 4-nitrobenzyloxycarbonyl, allyloxycarbonyl, 2,2,2-trichloroethoxycarbonyl, 2,2,2-tribromoethoxycarbonyl, aryloxycarbonyl, trimethylsilyl or t-butyldimethylsilyl group); alkoxy groups (preferably having from 1 to 6, more preferably from 1 to 3, carbon atoms, for example methoxy, ethoxy, propoxy or isopropoxy groups); carboxylic acyloxy groups (preferably $C_2-C_7$ alkanoyloxy groups, such as the acetoxy and propionyloxy groups); alkylsulfonyloxy and arylsulfonyloxy groups (particularly $C_1-C_6$, preferably $C_1-C_4$, alkylsulfonyloxy and $C_6-C_{10}$ carbocyclic arylsulfonyloxy groups, such as the methylsulfonyloxy, ethylsulfonyloxy, propylsulfonyloxy, benzenesulfonyloxy, naphthalenesulfonyloxy and p-toluenesulfonyloxy groups); the mercapto group; $C_1-C_6$, preferably $C_1-C_3$, alkylthio groups (for example the methylthio, ethylthio, propylthio or isopropylthio groups); the amino group; and carboxylic acylamino groups (particularly alkanoylamino groups preferably having from 2 to 7 carbon atoms, for example the acetamido, propionamido, butyramido or isobutyramido groups).

The compounds of the invention, being acids, are capable of forming salts and esters. The nature of such salts and esters is not critical to the present invention and the compounds of formula (I) are capable of forming salts and esters with any cations and ester-forming alcohols, respectively, which are known for the formation of salts and esters with compounds of this type. The only restriction on the nature of such salts and esters is that they should be "pharmaceutically acceptable" which means to those skilled in the art that the salt-forming cation or ester-forming alcohol should not, or should not to an unacceptable extent, reduce the activity of the compounds of formula (I), nor should they increase, or increase to an unacceptable extent, the toxicity of those compounds. However, the formation of salts and esters and the application of these criteria to the choice of salt-forming cations or ester-forming alcohols is so well-known to the man skilled in the art as to require no further definition here.

Examples of suitable esters include: $C_1-C_6$ preferably $C_1-C_4$, alkyl esters, such as the methyl, ethyl, propyl, isopropyl, butyl, isobutyl and t-butyl esters; $C_1-C_6$, preferably $C_1-C_4$, haloalkyl esters, which may have one or more halogen atoms (the maximum number of halogen atoms being dictated by the number of carbon atoms in the alkyl group, but preferably being from 1 to 3), such as the 2-iodoethyl, 2,2-dibromoethyl and 2,2,2-trichloroethyl esters; alkoxymethyl esters, wherein the alkoxy part has from 1 to 6, preferably from 1 to 4, carbon atoms, for example the methoxymethyl, propoxymethyl, isopropoxymethyl, butoxymethyl and isobutoxymethyl esters; aliphatic carboxylic acyloxymethyl esters, wherein the acyl part which may have saturated or unsaturated carbon-carbon bonds, preferably all saturated, has from 2 to 7, preferably from 2 to 5, carbon atoms, for example the acetoxymethyl, propionyloxymethyl, butyryloxymethyl, isobutyryloxymethyl and pivaloyloxymethyl esters; 1-alkoxycarbonyloxyethyl esters, where the alkoxy part has from 1 to 6, preferably from 1 to 4, carbon atoms, for example the 1-methoxycarbonyloxyethyl, 1-ethoxycarbonyloxyethyl, 1-propoxycarbonyloxyethyl, 1-isopropoxycarbonyloxyethyl, 1-butoxycarbonyloxyethyl and 1-isobutoxycarbonyloxyethyl esters; aralkyl esters, where the aryl part has from 6 to 10 ring carbon atoms and is unsubstituted or has one or more (preferably from 1 to 3) substituents selected from the group consisting of those substituents listed above as possible substituents on ring carbon atoms (and preferably $C_1-C_3$ alkoxy groups, nitro groups, $C_1-C_3$ alkyl groups, hydroxy groups and halogen atoms), for example the benzyl, p-methoxybenzyl, o-nitrobenzyl and p-nitrobenzyl esters; benzhydryl esters; (5-methyl-2-oxo-1,3-dioxolen-4-yl)methyl esters; and phthalidyl esters.

Esters of compounds of formula (I) which contain a suitable nitrogen-containing heterocyclic group represented by $R^3$ or in which any of the groups represented by $R^1$, $R^2$, $R^3$ and $R^4$ has a suitable amino substituent are capable of forming acid-addition salts. As with the salts and esters defined above, the nature of the acids employed to form these salts is not critical and is only limited, where the compounds of the invention are intended for pharmaceutical use, by the requirement that the resulting acid-addition salts should be pharmaceutically acceptable. Accordingly, a wide range of acids can be employed to form such acid-addition salts. Examples include: such mineral acids as hydrochloric acid and hydrobromic acid; and such organic acids as oxalic acid, tartaric acid and citric acid, preferably hydrochloric acid.

The compounds of formula (I) can also form salts with a wide variety of cations. Examples of salts which may be employed in the present invention include: metal salts, particularly alkali metal or alkaline earth metal salts, such as the lithium, sodium, potassium, calcium or magnesium salts; salts with basic amino acids, such as lysine or arginine; ammonium salts; and salts with organic amines, such as cyclohexylamine, diisopropylamine or triethylamine. Of these, the alkali metal, particularly sodium and potassium, salts are preferred.

The compounds of the invention can also exist in the form of hydrates and these likewise form part of the present invention.

Preferred compounds of the invention are those in which $R^3$ represents a ring-saturated nitrogen-containing heterocyclic group having from 4 to 8 ring atoms and having, in addition to the nitrogen atom specified, 0, 1 or 2 additional hetero-atoms selected from the group consisting of nitrogen, oxygen and sulfur atoms; or $R^3$ represents a group of formula:

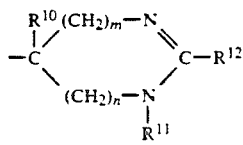

in which:

$R^{10}$ represents hydrogen or a $C_1$-$C_6$ alkyl group, preferably a $C_1$-$C_3$ alkyl group, for example a methyl or ethyl group;

$R^{11}$ represents hydrogen, a $C_1$-$C_6$, preferably $C_1$-$C_4$, alkyl group (such as a methyl, ethyl, propyl, isopropyl, butyl, isobutyl, sec-butyl or t-butyl group), an alkoxyalkyl group, in which the alkoxy part and the alkyl part each have from 1 to 6, preferably from 1 to 4, and more preferably 1 or 2, carbon atoms (for example the methoxymethyl, 1-ethoxyethyl and 2-ethoxyethyl groups), a $C_1$-$C_6$, preferably $C_1$-$C_3$ and more preferably $C_1$ or $C_2$, cyanoalkyl or haloalkyl group (for example a cyanomethyl or chloromethyl group), an aralkyl group where the aryl part is $C_6$-$C_{10}$ carbocyclic aryl and the alkyl part is $C_1$-$C_6$, preferably $C_1$-$C_3$, alkyl (for example a benzyl group) or a $C_3$-$C_8$ cycloalkyl group (for example a cyclopropyl, cyclobutyl, cyclopentyl, cyclohexyl, cycloheptyl or cyclooctyl group);

$R^{12}$ represents: hydrogen; a $C_1$-$C_6$, preferably $C_1$-$C_4$, alkyl group (for example a methyl, ethyl, propyl, isopropyl, butyl, isobutyl, sec-butyl or t-butyl group); a $C_3$-$C_8$, preferably $C_3$ or $C_4$, cycloalkyl group (for example a cyclopropyl, cyclobutyl, cyclopentyl, cyclohexyl or cycloheptyl group); an alkoxyalkyl group, in which the alkoxy part and the alkyl part each have from 1 to 6, preferably from 1 to 3, carbon atoms (for example a methoxymethyl, ethoxymethyl, propoxymethyl, isopropoxymethyl, 1-methoxyethyl or 2-methoxyethyl group); a cyanoalkyl group, in which the alkyl part is $C_1$-$C_6$, preferably $C_1$-$C_3$, alkyl (for example a cyanomethyl, 1-cyanoethyl, 2-cyanoethyl, 2-cyanopropyl or 1-methyl-2-cyanoethyl group); an alkoxycarbonylalkyl group in which the alkoxy part and the alkyl part each have from 1 to 6, preferably from 1 to 3, carbon atoms (for example a methoxycarbonylmethyl, ethoxycarbonylmethyl, 2-methoxycarbonylethyl or 2-ethoxycarbonylpropyl group); a $C_1$-$C_6$, preferably $C_1$-$C_3$, haloalkyl group (for example a chloromethyl, fluoromethyl, 2-fluoroethyl, 2-fluoropropyl, 1-methyl-2-fluoroethyl, trifluoromethyl or 2,2,2-trifluoroethyl group); an aromatic heterocyclic group having from 4 to 8 ring atoms, of which from 1 to 3 are hetero atoms selected from the group consisting of nitrogen, oxygen and sulfur atoms (for example a pyridyl, preferably 2-pyridyl or 3-pyridyl, thiazolyl, thienyl or oxazolyl group); or a phenyl group; and m is 0, 1, 2 or 3, more preferably 1 or 2 and most preferably 1, and n is 1, 2 or 3, more preferably 1 or 2 and most preferably 1, provided that (m+n) is an integer from 1 to 4.

The nitrogen-containing heterocyclic groups defined above for $R^3$ may be unsubstituted or may have one or more substituents selected from the group consisting of the substituents defined above for attachment to ring nitrogen atoms and the substituents defined above for attachment to ring carbon atoms. Particularly preferred nitrogen-containing heterocyclic groups include the 2-azetidinyl, 3-azetidinyl, 2-pyrrolidinyl, 3-pyrrolidinyl, 2-piperidyl, 3-piperidyl, 4-piperidyl, 2-morpholinyl, 5-thiazolidinyl, 1,4-thiazin-2-yl, hexahydropyrimidin-5-yl and hexahydropyridazin-4-yl groups, which may be substituted or unsubstituted. More particularly, we prefer compounds in which $R^3$ represents an azetidinyl (more preferably 3-azetidinyl) group or a pyrrolidinyl (more preferably 3-pyrrolidinyl) group, which may be unsubstituted or substituted as defined above, or a group of formula:

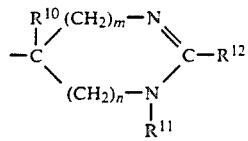

in which $R^{10}$, $R^{11}$, $R^{12}$, m and n are as defined above.

Most preferably, $R^3$ represents an unsubstituted or substituted 3-pyrrolidinyl group.

A preferred class of compounds of the present invention are those in which:

$R^1$ represents a methyl, ethyl, hydroxymethyl, methoxymethyl, methylthiomethyl, fluoromethyl, chloromethyl, methoxy, methylthio or trifluoromethyl group or a fluorine, chlorine or bromine atom;

$R^2$ represents a hydrogen, fluorine, chlorine or bromine atom or a methyl, ethyl, hydroxymethyl, methoxymethyl, methylthiomethyl, fluoromethyl, chloromethyl or trifluoromethyl group; or $R^1$ and $R^2$ together with the carbon atom to which they are attached form a 3- or 4-membered alicyclic ring;

$R^3$ represents a ring-saturated nitrogen-containing heterocyclic group having from 4 to 8 ring atoms, and having, in addition to the specified nitrogen atom, 0, 1 or 2 additional hetero atoms selected from the group consisting of nitrogen, oxygen and sulfur atoms and being unsubstituted or having from 1 to 3 substituents selected from the group consisting of (a) substituents attached to ring carbon atoms and (b) substituents attached to ring nitrogen atoms and (c) substituents attached to ring sulfur atoms:

(a) $C_1$–$C_6$, preferably $C_1$–$C_3$, alkyl groups, particularly the methyl, ethyl, propyl and isopropyl groups; alkoxyalkyl groups, in which the alkoxy part and the alkyl part each have from 1 to 6, preferably from 1 to 4, carbon atoms, particularly the methoxymethyl, ethoxymethyl, propoxymethyl, isopropoxymethyl, butoxymethyl, 1-methoxyethyl, 2-methoxyethyl, 3-methoxypropyl, 2-methoxypropyl and 4-ethoxybutyl groups; cyanoalkyl groups where the alkyl part has from 1 to 6, preferably from 1 to 4, carbon atoms, particularly the cyanomethyl, 1-cyanoethyl, 2-cyanoethyl, 3-cyanopropyl, 2-cyanopropyl and 4-cyanobutyl groups; $C_1$–$C_6$, preferably $C_1$–$C_3$, haloalkyl groups, particularly the trifluoromethyl, 2-fluoroethyl and 2,2,2-trifluoroethyl groups; $C_1$–$C_6$, particularly $C_1$–$C_3$, alkoxy groups, particularly the methoxy, ethoxy, propoxy and isopropoxy groups; the hydroxy group; halogen atoms, particularly the fluorine atom; $C_2$–$C_7$, particularly $C_2$–$C_5$ and more particularly $C_2$–$C_3$, aliphatic carboxylic acyloxy groups, particularly the acetoxy and propionyloxy groups; $C_1$–$C_6$, preferably $C_1$–$C_4$, alkylthio groups, particularly the methylthio, ethylthio, propylthio and isopropylthio groups; $C_1$–$C_6$, particularly $C_1$–$C_4$, alkylsulfonyl groups, particularly the methylsulfonyl, ethylsulfonyl, propylsulfonyl and isopropylsulfonyl groups; $C_1$–$C_6$, particularly $C_1$–$C_4$, alkylsulfinyl groups, particularly the methylsulfinyl, ethylsulfinyl, propylsulfinyl and isopropylsulfinyl groups; cyano groups; and carbamoyl groups;

(b) $C_1$–$C_6$, preferably $C_1$–$C_4$, alkyl groups, e.g. the methyl, ethyl, propyl, isopropyl, butyl, isobutyl, sec-butyl, t-butyl, pentyl, isopentyl and hexyl groups, particularly the methyl and ethyl groups; $C_1$–$C_6$, preferably $C_1$–$C_4$, hydroxyalkyl groups, particularly the 2-hydroxyethyl, 3-hydroxypropyl and 2-hydroxypropyl groups; $C_1$–$C_6$, particularly $C_1$–$C_3$, haloalkyl groups, such as the trifluoromethyl, 2-fluoroethyl and 2,2,2-trifluoroethyl groups; $C_1$–$C_7$ aliphatic acyl groups and their amino-acid analogs, such as the formyl, acetyl, propionyl, butyryl, isobutyryl, glycyl, alanyl and β-alanyl groups; aromatic-substituted aliphatic acyl groups, wherein the aromatic part is a $C_6$–$C_{10}$ carbocyclic aryl group and the aliphatic acyl part, which may be saturated or unsaturated is a $C_2$–$C_7$ aliphatic carboxylic acyl group, for example the phenylacetyl and cinnamoyl groups; the phenacyl group; the sulfo group; $C_1$–$C_6$, particularly $C_1$–$C_4$, alkylsulfonyl groups, particularly the methylsulfonyl, ethylsulfonyl, propylsulfonyl and isopropylsulfonyl groups; groups of formula —($R^5$)C=N—$R^6$, in which $R^5$ and $R^6$ are the same or different and each represents hydrogen, a $C_1$–$C_6$, preferably $C_1$–$C_3$, alkyl group (particularly methyl or ethyl), the phenyl group, an aromatic heterocyclic group (particularly a pyridyl or furyl group), the methoxymethyl group, the cyanomethyl group, the benzyl group, the fluoromethyl group or the chloromethyl group); or the carbamoyl group;

(c) oxygen atoms;
or a group of formula:

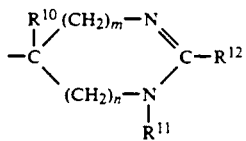

in which:

$R^{10}$ represents hydrogen or methyl;

$R^{11}$ represents hydrogen; a $C_1$–$C_3$ alkyl group (i.e. methyl, ethyl, propyl or isopropyl), a $C_3$–$C_6$ cycloalkyl group (preferably cyclopropyl or cyclobutyl), an alkoxyalkyl group wherein the alkoxy part and the alkyl part both have from 1 to 3 carbon atoms (particularly methoxymethyl, 1-ethoxyethyl or 2-ethoxyethyl), cyanomethyl, chloromethyl, fluoromethyl or benzyl;

$R^{12}$ represents hydrogen, a $C_1$–$C^3$ alkyl group (i.e. methyl, ethyl, propyl or isopropyl), a $C_3$–$C_6$ cycloalkyl group (preferably cyclopropyl or cyclobutyl), an alkoxyalkyl group wherein the alkoxy part and the alkyl part both have from 1 to 3 carbon atoms (preferably methoxymethyl or ethoxymethyl), a cyanoalkyl group, wherein the alkyl part has from 1 to 3 carbon atoms (preferably cyanomethyl, 1-cyanoethyl or 2-cyanoethyl), phenyl or an aromatic heterocyclic group (preferably 2-pyridyl or 3-pyridyl) and m and n are each 1 or 2;

$R^4$ represents hydrogen, ethyl, ethyl having at its α-position a substituent selected from the group consisting of:

hydroxy groups, amino groups, $C_1$–$C_7$ aliphatic acyloxy groups and $C_1$–$C_7$ aliphatic acylamino groups;

(for example α-hydroxyethyl, α-acetoxyethyl, α-propionyloxyethyl, α-butyryloxyethyl, α-aminoethyl, α-acetamidoethyl, α-propionamidoethyl or α-butyramidoethyl), isopropyl, isopropyl having at its α-position a substituent selected from the group consisting of:

hydroxy groups, amino groups, $C_1$–$C_7$ aliphatic acyloxy groups and $C_1$–$C_7$ aliphatic acylamino groups;

(for example 1-hydroxy-1-methylethyl, 1-acetoxy-1-methylethyl, 1-propionyloxy-1-methylethyl, 1-butyryloxy-1-methylethyl, 1-amino-1-methylethyl, 1-acetamido-1-methylethyl, 1-propionamido-1-methylethyl or 1-butyramido-1-methylethyl) or methoxy and pivaloyloxymethyl and (5-methyl-2-oxo-1,3-dioxolen-4-yl)methyl esters thereof and hydrochloric acid addition salts of said esters; and sodium and potassium salts thereof.

The most preferred compounds of the present invention are those in which:

$R^1$ represents methyl, ethyl, trifluoromethyl, fluoromethyl, chloromethyl, methoxymethyl, methylthio, hydroxymethyl, phenyl, benzyl, fluorine, chlorine or bromine;

$R^2$ represents hydrogen, methyl, fluorine or chlorine; or $R^1$ and $R^2$, together with the carbon atom to which they are attached, form a cyclopropane ring;

$R^3$ represents a 3-pyrrolidinyl or 3-azetidinyl group which is unsubstituted or has from 1 to 3 substituents selected from the group consisting of (a) substituents on ring carbon atoms and (b) substituents on ring nitrogen atoms;

(a) methyl, methoxy, fluorine, methylthio, methylsulfinyl, methylsulfonyl, hydroxymethyl, $C_2$–$C_7$ alkoxycarbonyl, cyano, carbamoyl or acyloxymethyl wherein the acyl part is $C_1$-$C_5$ aliphatic acyl;

(b) formyl, acetyl, glycyl, alanyl, formimidoyl, acetimidoyl, propionimidoyl or α-methoxyacetimidoyl; or a 3,4,5,6-tetrahydropyrimidin-5-yl group having at its 3-position hydrogen or methyl and having at its 2-position hydrogen, methyl, ethyl, isopropyl, methoxymethyl, cyanomethyl, fluoromethyl, pyridyl or benzyl; and $R^4$ represents α-hydroxyethyl.

The compounds of the present invention can exist in the form of various optical isomers and stereoisomers due to the presence of asymmetric carbon atoms. Although all of these isomers are represented herein by a single formula, it should be understood that the present invention envisages both the individual isolated isomers, as well as mixtures of isomers. Preferred compounds are those in which the carbon atom at the 5-position is in the same configuration as in thienamycin, that is to say the R-configuration. In particular, we prefer compounds having the (5R, 6S) or (5R, 6R) configuration and, when the group represented by $R^4$ has a substituent at its α-position (for example a hydroxy, acetoxy, amino or acetamido group), the preferred configuration of this group is the R-configuration.

In the preferred compounds of the invention, $R^1$ represents one of the groups defined above, most preferably a methyl group, whilst $R^2$ represents a hydrogen atom. In this case, the group, particularly methyl group, represented by $R^1$ is preferably in the R-configuration (also known as the "β configuration"). We have found that those compounds having a 1-methyl group in the R-configuration have surprisingly superior activity.

Examples of preferred compounds of the invention are given in the following list; in this list, the configuration of substituents is not specified and each of the compounds given in this list may be in any of the possible configurations or may be a mixture of isomers; however, the listed compounds are preferably (5R, 6S) or (5R, 6R), more preferably (1R, 5R, 6S) or (1R, 5R, 6R) and, where $R^4$ (the group at the 6-position) has an α-substituent, this is preferably in the R-configuration.

1. 2-(1-formylazetidin-3-ylthio)-6-(1-hydroxyethyl)-1-methylcarbapen-2-em-3-carboxylic acid
2. 2-(1-formylpyrrolidin-3-ylthio)-6-(1-hydroxyethyl)-1-methylcarbapen-2-em-3-carboxylic acid
3. 2-(1-formylpiperidin-4-ylthio)-6-(1-hydroxyethyl)-1-methylcarbapen-2-em-3-carboxylic acid
4. 2-(1-acetylazetidin-3-ylthio)-6-(1-hydroxyethyl)-1-methylcarbapen-2-em-3-carboxylic acid
5. 2-(1-acetylpyrrolidin-3-ylthio)-6-(1-hydroxyethyl)-1-methylcarbapen-2-em-3-carboxylic acid
6. 2-(1-acetylpiperidin-4-ylthio)-6-(1-hydroxyethyl)-1-methylcarbapen-2-em-3-carboxylic acid
7. 2-(1-glycylazetidin-3-ylthio)-6-(1-hydroxyethyl)-1-methylcarbapen-2-em-3-carboxylic acid
8. 2-(1-glycylpyrrolidin-3-ylthio)-6-(1-hydroxyethyl)-1-methylcarbapen-2-em-3-carboxylic acid
9. 2-[1-(β-alanyl)pyrrolidin-3-ylthio]-6-(1-hydroxyethyl)-1-methylcarbapen-2-em-3-carboxylic acid
10. 2-(1-alanylpyrrolidin-3-ylthio)-6-(1-hydroxyethyl)-1-methylcarbapen-2-em-3-carboxylic acid
11. pivaloyloxymethyl 2-(1-formylpyrrolidin-3-ylthio)-6-(1-hydroxyethyl)-1-methylcarbapen-2-em-3-carboxylate
12. pivaloyloxymethyl 2-(1-acetylpyrrolidin-3-ylthio)-6-(1-hydroxyethyl)-1-methylcarbapen-2-em-3-carboxylate
13. pivaloyloxymethyl 2-(1-glycylpyrrolidin-3-ylthio)-6-(1-hydroxyethyl)-1-methylcarbapen-2-em-3-carboxylate
14. 6-(1-hydroxyethyl)-1-methyl-2-(pyrrolidin-3-ylthio)carbapen-2-em-3-carboxylic acid
15. 6-(1-hydroxyethyl)-2-[1-(2-hydroxyethyl)pyrrolidin-3-ylthio]-1-methylcarbapen-2-em-3-carboxylic acid
16. 2-[1-(2-fluoroethyl)pyrrolidin-3-ylthio]-6-(1-hydroxyethyl)-1-methylcarbapen-2-em-3-carboxylic acid
17. 6-(1-hydroxyethyl)-1-methyl-2-(1-phenylacetylpyrrolidin-3-ylthio)carbapen-2-em-3-carboxylic acid
18. 6-(1-hydroxyethyl)-1-methyl-2-(1-sulfopyrrolidin-3-ylthio)carbapen-2-em-3-carboxylic acid
19. 6-(1-hydroxyethyl)-2-(1-methanesulfonylpyrrolidin-3-ylthio)-1-methylcarbapen-2-em-3-carboxylic acid
20. 2-(1-carbamoylpyrrolidin-3-ylthio)-6-(1-hydroxyethyl)-1-methylcarbapen-2-em-3-carboxylic acid
21. 6-(1-hydroxyethyl)-1-methyl-2-(1-phenacylpyrrolidin-3-ylthio)carbapen-2-em-3-carboxylic acid
22. 2-(1-formimidoylpyrrolidin-3-ylthio)-6-(1-hydroxyethyl)-1-methylcarbapen-2-em-3-carboxylic acid
23. 2-(1-acetimidoylpyrrolidin-3-ylthio)-6-(1-hydroxyethyl)-1-methylcarbapen-2-em-3-carboxylic acid
24. 6-(1-hydroxyethyl)-2-(4-methoxypyrrolidin-3-ylthio)-1-methylcarbapen-2-em-3-carboxylic acid
25. 2-(1-formyl-4-methoxypyrrolidin-3-ylthio)-6-(1-hydroxyethyl)-1-methylcarbapen-2-em-3-carboxylic acid
26. 2-(1-acetyl-4-methoxypyrrolidin-3-ylthio)-6-(1-hydroxyethyl)-1-methylcarbapen-2-em-3-carboxylic acid
27. 2-(1-formimidoyl-4-methoxypyrrolidin-3-ylthio)-6-(1-hydroxyethyl)-1-methylcarbapen-2-em-3-carboxylic acid
28. 2-(1-acetimidoyl-4-methoxypyrrolidin-3-ylthio)-6-(1-hydroxyethyl)-1-methylcarbapen-2-em-3-carboxylic acid
29. 6-(1-hydroxyethyl)-1-methyl-2-(5-methylpyrrolidin-3-ylthio)carbapen-2-em-3-carboxylic acid
30. 2-(1-formyl-5-methylpyrrolidin-3-ylthio)-6-(1-hydroxyethyl)-1-methylcarbapen-2-em-3-carboxylic acid
31. 2-(1-acetyl-5-methylpyrrolidin-3-ylthio)-6-(1-hydroxyethyl)-1-methylcarbapen-2-em-3-carboxylic acid
32. 2-(1-acetimidoyl-4-methylpyrrolidin-3-ylthio)-6-(1-hydroxyethyl)-1-methylcarbapen-2-em-3-carboxylic acid
33. 2-(4-acetoxypyrrolidin-3-ylthio)-6-(1-hydroxyethyl)-1-methylcarbapen-2-em-3-carboxylic acid
34. 2-(4-acetoxy-1-acetylpyrrolidin-3-ylthio)-6-(1-hydroxyethyl)-1-methylcarbapen-2-em-3-carboxylic acid
35. 2-(1-acetimidoyl-4-acetoxypyrrolidin-3-ylthio)-6-(1-hydroxyethyl)-1-methylcarbapen-2-em-3-carboxylic acid
36. 2-(4-fluoropyrrolidin-3-ylthio)-6-(1-hydroxyethyl)-1-methylcarbapen-2-em-3-carboxylic acid
37. 2-(1-acetyl-4-fluoropyrrolidin-3-ylthio)-6-(1-hydroxyethyl)-1-methylcarbapen-2-em-3-carboxylic acid
38. 2-(1-acetimidoyl-4-fluoropyrrolidin-3-ylthio)-6-(1-hydroxyethyl)-1-methylcarbapen-2-em-3-carboxylic acid
39. 6-(1-hydroxyethyl)-1-methyl-2-(4-methylthiopyrrolidin-3-ylthio)carbapen-2-em-3-carboxylic acid 40. 2-(1-acetyl-4-methylthiopyrrolidin-3-ylthio)-6-(1-hydroxyethyl)-1-methylcarbapen-2-em-3-carboxylic acid
41. 2-(1-acetimidoyl-4-methylthiopyrrolidin-3-ylthio)-6-(1-hydroxyethyl)-1-methylcarbapen-2-em-3-carboxylic acid
42. 6-(1-hydroxyethyl)-2-(4-methanesulfinylpyrrolidin-3-ylthio)-1-methylcarbapen-2-em-3-carboxylic acid
43. 2-(1-acetyl-4-methanesulfinylpyrrolidin-3-ylthio)-6-(1-hydroxyethyl)-1-methylcarbapen-2-em-3-carboxylic acid
44. 2-(1-acetimidoyl-4-methanesulfinylpyrrolidin-3-ylthio)-6-(1-hydroxyethyl)-1-methylcarbapen-2-em-3-carboxylic acid
45. 6-(1-hydroxyethyl)-2-(4-methanesulfonylpyrrolidin-3-ylthio)-1-methylcarbapen-2-em-3-carboxylic acid
46. 2-(1-acetyl-4-methanesulfonylpyrrolidin-3-ylthio)-6-(1-hydroxyethyl)-1-methylcarbapen-2-em-3-carboxylic acid
47. 2-(1-acetimidoyl-4-methanesulfonylpyrrolidin-3-ylthio)-6-(1-hydroxyethyl)-1-methylcarbapen-2-em-3-carboxylic acid
48. 6-(1-hydroxyethyl)-2-(4-hydroxypyrrolidin-3-ylthio)-1-methylcarbapen-2-em-3-carboxylic acid
49. 2-(1-acetyl-4-hydroxypyrrolidin-3-ylthio)-6-(1-hydroxyethyl)-1-methylcarbapen-2-em-3-carboxylic acid
50. 2-(1-acetimidoyl-4-hydroxypyrrolidin-3-ylthio)-6-(1-hydroxyethyl)-1-methylcarbapen-2-em-3-carboxylic acid
51. pivaloyloxymethyl 2-(1-acetyl-4-methoxypyrrolidin-3-ylthio)-6-(1-hydroxyethyl)-1-methylcarbapen-2-em-3-carboxylate
52. pivaloyloxymethyl 2-(1-acetimidoyl-4-methoxypyrrolidin-3-ylthio)-6-(1-hydroxyethyl)-1-methylcarbapen-2-em-3-carboxylate
53. pivaloyloxymethyl 6-(1-hydroxyethyl)-1-methyl-2-(pyrrolidin-3-ylthio)carbapen-2-em-3-carboxylate
54. pivaloyloxymethyl 2-(1-acetimidoylpyrrolidin-3-ylthio)-6-(1-hydroxyethyl)-1-methylcarbapen-2-em-3-carboxylate
55. pivaloyloxymethyl 2-(1-acetyl-4-methoxypyrrolidin-3-ylthio)-6-(1-hydroxyethyl)-1-methylcarbapen-2-em-3-carboxylate
56. pivaloyloxymethyl 2-(1-acetimidoyl-4-methoxypyrrolidin-3-ylthio)-6-(1-hydroxyethyl)-1-methylcarbapen-2-em-3-carboxylate
57. 2-(1-acetimidoyl-5-chloromethylpyrrolidin-3-ylthio)-6-(1-hydroxyethyl)-1-methylcarbapen-2-em-3-carboxylic acid
58. 2-(1-acetimidoyl-5-fluoromethylpyrrolidin-3-ylthio)-6-(1-hydroxyethyl)-1-methylcarbapen-2-em-3-carboxylic acid
59. 2-(5-carbamoyl-1-formimidoylpyrrolidin-3-ylthio)-6-(1-hydroxyethyl)-1-methylcarbapen-2-em-3-carboxylic acid
60. 2-(1-formimidoyl-5-methoxycarbonylpyrrolidin-3-ylthio)-6-(1-hydroxyethyl)-1-methylcarbapen-2-em-3-carboxylic acid
61. 2-(5-acetoxymethyl-1-formimidoylpyrrolidin-3-ylthio)-6-(1-hydroxyethyl)-1-methylcarbapen-2-em-3-carboxylic acid
62. 6-(1-hydroxyethyl)-2-(4-methoxypiperidin-3-ylthio)-1-methylcarbapen-2-em-3-carboxylic acid
63. 2-(1-acetyl-4-methoxypiperidin-3-ylthio)-6-(1-hydroxyethyl)-1-methylcarbapen-2-em-3-carboxylic acid
64. 6-(1-hydroxyethyl)-2-(4-methoxyperhydroazocin-3-ylthio)-1-methylcarbapen-2-em-3-carboxylic acid
65. 6-(1-hydroxyethyl)-2-(4-methoxyperhydroazepin-3-ylthio)-1-methylcarbapen-2-em-3-carboxylic acid
66. (5-methyl-2-oxo-1,3-dioxolen-4-yl)methyl 2-(1-acetimidoylpyrrolidin-3-ylthio)-6-(1-hydroxyethyl)-1-methylcarbapen-2-em-3-carboxylate
67. (5-methyl-2-oxo-1,3-dioxolen-4-yl)methyl 2-(1-acetylpyrrolidin-3-ylthio)-6-(1-hydroxyethyl)-1-methylcarbapen-2-em-3-carboxylate
68. 6-(1-hydroxyethyl)-1-methyl-2-[1-(N-methylformimidoyl)azetidin-3-ylthio]carbapen-2-em-3-carboxylic acid
69. 6-(1-hydroxyethyl)-1-methyl-2-[1-(N-methylacetimidoyl)azetidin-3-ylthio]carbapen-2-em-3-carboxylic acid
70. 6-(1-hydroxyethyl)-1-methyl-2-[1-(N-methylformimidoyl)pyrrolidin-3-ylthio]carbapen-2-em-3-carboxylic acid
71. 6-(1-hydroxyethyl)-1-methyl-2-[1-(N-methylacetimidoyl)pyrrolidin-3-ylthio]carbapen-2-em-3-carboxylic acid
72. 6-(1-hydroxyethyl)-2-(5-methoxycarbonylpyrrolidin-3-ylthio) 1-methylcarbapen-2-em-3-carboxylic acid
73. 6-(1-hydroxyethyl)-2-(5-hydroxymethylpyrrolidin-3-ylthio)-1-methylcarbapen-2-em-3-carboxylic acid
74. 2-(5-acetoxymethylpyrrolidin-3-ylthio)-6-(1-hydroxyethyl)-1-methylcarbapen-2-em-3-carboxylic acid
75. 2-(5-carbamoylpyrrolidin-3-ylthio)-6-(1-hydroxyethyl)-1-methylcarbapen-2-em-3-carboxylic acid
76. 2-(1-acetimidoyl-5-methoxycarbonylpyrrolidin-3-ylthio)-6-(1-hydroxyethyl)-1-methylcarbapen-2-em-3-carboxylic acid
77. 2-(1-acetimidoyl-5-hydroxymethylpyrrolidin-3-ylthio)-6-(1-hydroxyethyl)-1-methylcarbapen-2-em-3-carboxylic acid
78. 2-(1-acetimidoyl-5-acetoxymethylpyrrolidin-3-ylthio)-6-(1-hydroxyethyl)-1-methylcarbapen-2-em-3-carboxylic acid
79. 2-(1-acetimidoyl-5-carbamoylpyrrolidin-3-ylthio)-6-(1-hydroxyethyl)-1-methylcarbapen-2-em-3-carboxylic acid
80. 6-(1-hydroxyethyl)-1-methyl-2-(1-propionimidoylpyrrolidin-3-ylthio)carbapen-2-em-3-carboxylic acid
81. 6-(1-hydroxyethyl)-2-[1-(α-methoxyacetimidoyl)azetidin-3-ylthio]-1-methylcarbapen-2-em-3-carboxylic acid
82. 2-(1-acetimidoylpyrrolidin-3-ylthio)-6-(1-hydroxyethyl)-1-trifluoromethylcarbapen-2-em-3-carboxylic acid
83. 2-(1-acetimidoylpyrrolidin-3-ylthio)-1-ethyl-6-(1-hydroxyethyl)carbapen-2-em-3-carboxylic acid
84. 2-(1-acetimidoylpyrrolidin-3-ylthio)-6-(1-hydroxyethyl)-1-methoxycarbapen-2-em-3-carboxylic acid
85. 2-(1-acetimidoylpyrrolidin-3-ylthio)-6-(1-hydroxyethyl)-1-methylthiocarbapen-2-em-3-carboxylic acid
86. 6-(1-hydroxyethyl)-2-[1-(α-fluoroacetimidoyl)azetidin-3-ylthio]-1-methylcarbapen-2-em-3-carboxylic acid
87. 6-(1-hydroxyethyl)-1-methyl-2-(3,4,5,6-tetrahydropyrimidin-5-ylthio)carbapen-2-em-3-carboxylic acid
88. 6-(1-hydroxyethyl)-1-methyl-2-(2-methyl-3,4,5,6-tetrahydropyrimidin-5-ylthio)carbapen-2-em-3-carboxylic acid 89. 2-(2-ethyl-3,4,5,6-tetrahydropyrimidin-5-ylthio)-6-(1-hydroxyethyl)-1-methylcarbapen-2-em-3-carboxylic acid
90. 6-(1-hydroxyethyl)-2-(2-methoxymethyl-3,4,5,6-tetrahydropyrimidin-5-ylthio)-1-methylcarbapen-2-em-3-carboxylic acid
91. 2-(2-cyanomethyl-3,4,5,6-tetrahydropyrimidin-5-ylthio)-6-(1-hydroxyethyl)-1-methylcarbapen-2-em-3-carboxylic acid
92. 2-(2-benzyl-3,4,5,6-tetrahydropyrimidin-5-ylthio)-6-(1-hydroxyethyl)-1-methylcarbapen-2-em-3-carboxylic acid
93. 2-(2,3-dimethyl-3,4,5,6-tetrahydropyrimidin-5-ylthio)-6-(1-hydroxyethyl)-1-methylcarbapen-2-em-3-carboxylic acid
94. 6-(1-hydroxyethyl)-2-(2-isopropyl-3,4,5,6-tetrahydropyrimidin-5-ylthio)-1-methylcarbapen-2-em-3-carboxylic acid
95. 6-(1-hydroxyethyl)-2-(2-methoxymethyl-3-methyl-3,4,5,6-tetrahydropyrimidin-5-ylthio)-1-methylcarbapen-2-em-3-carboxylic acid
96. 2-(2-fluoromethyl-3,4,5,6-tetrahydropyrimidin-5-ylthio)-6-(1-hydroxyethyl)-1-methylcarbapen-2-em-3-carboxylic acid
97. 2-(1-acetimidoylpyrrolidin-3-ylthio)-6-(1-hydroxyethyl)-1,1-dimethylcarbapen-2-em-3-carboxylic acid
98. 6-(1-hydroxyethyl)-1,1-dimethyl-2-(1-propionimidoylpyrrolidin-3-ylthio)carbapen-2-em-3-carboxylic acid
99. 6-(1-hydroxyethyl)-2-[1-(α-methoxyacetimidoyl)pyrrolidin-3-ylthio]-1,1-dimethylcarbapen-2-em-3-carboxylic acid
100. 2-(1-formimidoylpyrrolidin-3-ylthio)-6-(1-hydroxyethyl)-1,1-dimethylcarbapen-2-em-3-carboxylic acid
101. 2-(1-acetimidoylpyrrolidin-3-ylthio)-1,1-dichloro-6-(1-hydroxyethyl)carbapen-2-em-3-carboxylic acid
102. 2-(1-acetimidoylpyrrolidin-3-ylthio)-1-chloro-6-(1-hydroxyethyl)carbapen-2-em-3-carboxylic acid
103. 6-(1-hydroxyethyl)-1-methyl-2-(1-nicotinimidoyl-pyrrolidin-3-ylthio)carbapen-2-em-3-carboxylic acid
104. 6-(1-hydroxyethyl)-1,1-dimethyl-2-(2-methyl 3,4,5,6-tetrahydropyrimidin-5-ylthio)carbapen-2-em-3-carboxylic acid
105. 2-(1-acetimidoylpyrrolidin-3ylthio)-6-(1-hydroxyethyl)-(carbapen-2-em)-1-spiro-1'-cyclopropane-3-carboxylic acid
106. 6-(1-hydroxyethyl)-1-methyl-2-(1-methylpyrrolidin-3-ylthio)carbapen-2-em-3-carboxylic acid
107. 2-(1-ethoxycarbonylmethylpyrrolidin-3-ylthio)-6-(1-hydroxyethyl)-1-methylcarbapen-2-em-3-carboxylic acid
108. 2-(5-carbamoyl-1-methylpyrrolidin-3-ylthio)-6-(1-hydroxyethyl)-1-methylcarbapen-2-em-3-carboxylic acid
109. 2-(1-acetimidoylpyrrolidin-3-ylthio)-1-fluoro-6-(1-hydroxyethyl)carbapen-2-em-3-carboxylic acid
110. 6-(1-hydroxyethyl)-1-methoxy-2-(pyrrolidin-3-ylthio)carbapen-2-em-3-carboxylic acid
111. 2-(1-acetimidoylpyrrolidin-3-ylthio)-1-cyano-6-(1-hydroxyethyl)carbapen-2-em-3-carboxylic acid
112. 1-ethoxycarbonyl-6-(1-hydroxyethyl)-2-(pyrrolidin-3-ylthio)carbapen-2-em-3-carboxylic acid
113. 2-(1-acetimidoylpyrrolidin-3-ylthio)-1,1-difluoro-6-(1-hydroxyethyl)carbapen-2-em-3-carboxylic acid
114. 1,1-difluoro-6-(1-hydroxyethyl)-2-(pyrrolidin-3-ylthio)carbapen-2-em-3-carboxylic acid
115. p-nitrobenzyl 6-(1-hydroxyethyl)-1-methyl-2-[1-(N-p-nitrobenzyloxycarbonylacetimidoyl)pyrrolidin-3-ylthio]carbapen-2-em-3-carboxylate
116. p-nitrobenzyl 6-(1-hydroxyethyl)-1-methyl-2-[1-(p-nitrobenzyloxycarbonyl)pyrrolidin-3-ylthio]carbapen-2-em-3-carboxylate
117. p-nitrobenzyl 2-[5-carbamoyl-1-(p-nitrobenzyloxycarbonyl)pyrrolidin-3-ylthio]-6-(1-hydroxyethyl)-1-methylcarbapen-2-em-3-carboxylate
118. p-nitrobenzyl 6-(1-hydroxyethyl)-1-methoxy-2-[1-(p-nitrobenzyloxycarbonyl)pyrrolidin-3-yl]carbapen-2-em-3-carboxylate
119. p-nitrobenzyl 6-(1-hydroxyethyl)-1-methoxy-2-[1-(N-p-nitrobenzyloxycarbonylacetimidoyl)pyrrolidin-3-ylthio]carbapen- 2-em-3- carboxylate
120. p-nitrobenzyl 1-fluoro-6-(1-hydroxyethyl)-2-[1-(N-p-nitrobenzyloxycarbonylacetimidoyl)pyrrolidin-3-ylthio]carbapen-2-em-3-carboxylate
121. p-nitrobenzyl 2-[5-carbamoyl-1-(N-p-nitrobenzyloxycarbonylacetimidoyl)pyrrolidin-3-ylthio]-6-(1-hydroxyethyl)-1-methylcarbapen-2-em-3- carboxylate
122. p-nitrobenzyl 6-(1-hydroxyethyl)-1,1-dimethyl-2-[1-(p-nitrobenzyloxycarbonyl)pyrrolidin-3-ylthio]carbapen-2-em-3-carboxylate
123. 6-(1-hydroxyethyl)-1,1-dimethyl-2-pyrrolidin-3-ylthio)carbapen-2-em-3-carboxylic acid
124. p-nitrobenzyl 1-methyl-2-[1-(p-nitrobenzyl-oxycarbonyl)pyrrolidin-3-ylthio]-6-[1-(trimethylsilyloxy)ethyl]carbapen-2-em-3-carboxylate
125. p-nitrobenzyl 1-methyl-2-{1-[N-(p-nitrobenzyloxycarbonyl)acetimidoyl]pyrrolidin-3-ylthio}-6-[1-(trimethylsilyloxy)ethyl]carbapen-2-em-3-carboxylate
126. 2-(1-acetimidoyl-5-cyanopyrrolidin-3-ylthio)-6-C1-hydroxyethyl)-1-methylcarbapen-2-em-3-carboxylic acid Of the compounds listed above, the preferred compounds are Compounds Nos. 23 and 79, and particularly those isomers of these Compounds having the 6-[1(R)-hydroxyethyl] and (5R, 6S) or (5R, 6R) configurations, more preferably (1R, 5R, 6S) or (1R, 5R, 6R) configurations, as well as pharmaceutically acceptable salts and esters thereof.

The compounds of the invention may be prepared by:
(a) reacting a compound of formula (II):

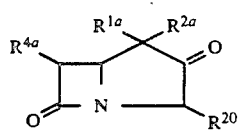

(in which $R^{1a}$, $R^{2a}$ $R^{4a}$ represent any one of the groups or atoms defined for $R^1$, $R^2$ and $R^4$, respectively, or any such group in which any reactive group is protected, and $R^{20}$ represents a carboxy group or a protected carboxy group) with a compound of formula (IIa)

$$R^{21}OH \qquad (IIa)$$

(in which $R^{21}$ represents an alkanesulfonyl group, an arylsulfonyl group, a dialkylphosphoryl group or a diarylphosphoryl group) or with an active derivative (e.g. anhydride or halide) of said compound (IIa), to give a compound of formula (III):

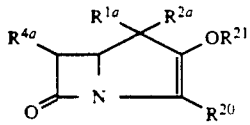

(III)

(in which $R^{1a}$, $R^{2a}$, $R^{4a}$, $R^{20}$ and $R^{21}$ are as defined above);

(b) reacting said compound of formula (III) with a compound of formula (IIIa):

$R^{3a}SH$ (IIIa)

(in which $R^{3a}$ represents any one of the groups represented by $R^3$ or any such group in which any active group is protected) to give a compound of formula (IV):

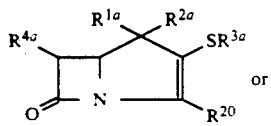

(IV)

or (c) reacting said compound of formula (III) with a compound of formula (V):

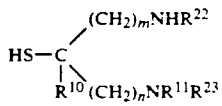

(V)

(in which m, n, $R^{10}$ and $R^{11}$ are as defined above and $R^{22}$ and $R^{23}$ are nitrogen-protecting groups) to give a compound of formula (VI):

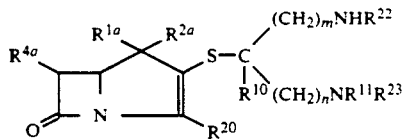

(VI)

(in which $R^{1a}$, $R^{2a}$, $R^{4a}$, $R^{10}$, $R^{11}$, $R^{20}$, $R^{22}$, $R^{23}$, m and n are as defined above):

(d) removing from said compound of formula (VI) the protecting groups represented by $R^{22}$ and $R^{23}$ and reacting the product thereof with a compound of formula (VIa):

$R^{24}O-C(R^{12})=NH$ (VIa)

(in which $R^{12}$ is as defined above and $R^{24}$ represents an alkyl or aralkyl group); to give a compound of formula (XIV):

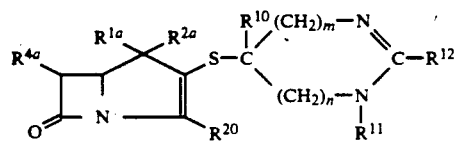

(XIV)

(in which $R^{1a}$, $R^{2a}$, $R^{4a}$, $R^{10}$, $R^{11}$, $R^{12}$, $R^{20}$, m and n are as defined above:

(e) if necessary, removing protecting groups from said compounds of formulae (IV) and (XIV) to give a compound of formula, respectively, (I) or (Ia):

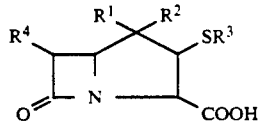

(I)

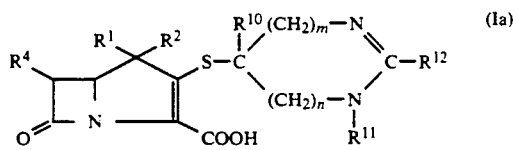

(Ia)

(in which $R^1$, $R^2$, $R^3$, $R^4$, $R^{10}$, $R^{11}$, $R^{12}$, m and n are as defined above)
or an ester thereof; and (f) if necessary, salifying or esterifying said compound of formula (I) or (Ia).

Alternatively, the compounds of the invention may be prepared by the following process:

(a) reacting a compound of formula (VIII):

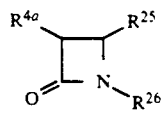

(VII)

(in which $R^{4a}$ is as defined above, $R^{25}$ represents an aliphatic acyloxy group, preferably an acetoxy group, and $R^{26}$ represents a leaving group, preferably a trimethylxilyl group) with a compound of formula (VIII):

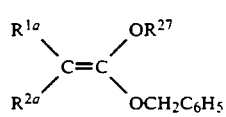

(VIII)

(in which $R^{1a}$ and $R^{2a}$ are as defined above and $R^{27}$ represents a leaving group, preferably a trimethylsilyl group), to give a compound of formula (IX):

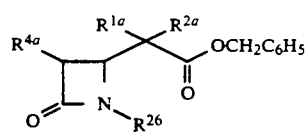

(IX)

(in which $R^{1a}$, $R^{2a}$, $R^{4a}$ and $R^{26}$ are as defined above):

(b) reacting said compound of formula (IX) first with water and then with a hydrogenating agent (preferably hydrogen in the presence of a hydrogenation catalyst, such as palladium-on-charcoal) to give a compound of formula (X):

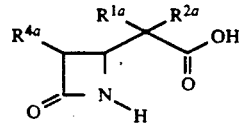

(X)

(in which $R^{1a}$, $R^{2a}$ and $R^{4a}$ are as defined above):

(c) reacting said compound of formula (X) with a compound of formula (IIIa):

$R^{3a}$—SH (IIIa)

(in which $R^{3a}$ is as defined above) or with an active derivative, such as an alkali metal salt thereof, to give a compound of formula (XI):

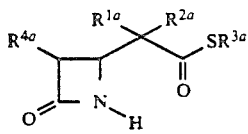 (XI)

(in which $R^{1a}$, $R^{2a}$, $R^{3a}$ and $R^{4a}$ are as defined above):

(d) reacting said compound of formula (XI) with an oxalic acid derivative of formula (XIa):

$R^{20}$—C(=O)—Hal (XIa)

(in which $R^{20}$ is as defined above and Hal represents a halogen atom, preferably a chlorine atom) to give a compound of formula (XII):

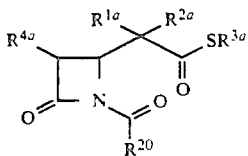 (XII)

(in which $R^{1a}$, $R^{2a}$, $R^{3a}$, $R^{4a}$ and $R^{20}$ are as defined above):

(e) reacting said compound of formula (XII) with a compound of formula (XIIa):

$P(R^{27})_3$ (XIIa)

(in which $R^{27}$ represents an alkoxy group, preferably a $C_1$-$C_6$ alkoxy group, an aralkoxy group, in which the aryl part is preferably a $C_6$-$C_{10}$ carbocyclic aryl group which is unsubstituted or has one or more substituents selected from the group consisting of the substituents listed above as possible substituents on carbon atoms, a dialkylamino group, in which each alkyl part has from 1 to 6 carbon atoms, or a diarylamino group, in which each aryl part is a $C_6$-$C_{10}$ carbocyclic aryl group which is unsubstituted or has one or more substituents selected from the group consisting of those substituents listed above as possible substituents on ring carbon atoms) to give a compound of formula (XIII):

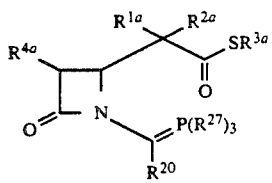 (XIII)

(in which $R^{1a}$, $R^{2a}$, $R^{3a}$, $R^{4a}$ and $R^{27}$ are as defined above):

(f) cyclizing said compound of formula (XIII) to give a compound of formula (IV):

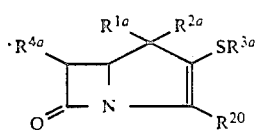 (IV)

(in which $R^{1a}$, $R^{2a}$, $R^{3a}$, $R^{4a}$ and $R^{20}$ are as defined above);

(g) if necessary, removing protecting groups from said compound of formula (IV);

(h) if necessary, salifying or esterifying the product of step (f) or (g).

Preparation of the compounds of the invention is described in more detail in the following Methods.

METHOD A

In this Method, compounds of formula (I) are prepared as illustrated in the following reaction scheme:

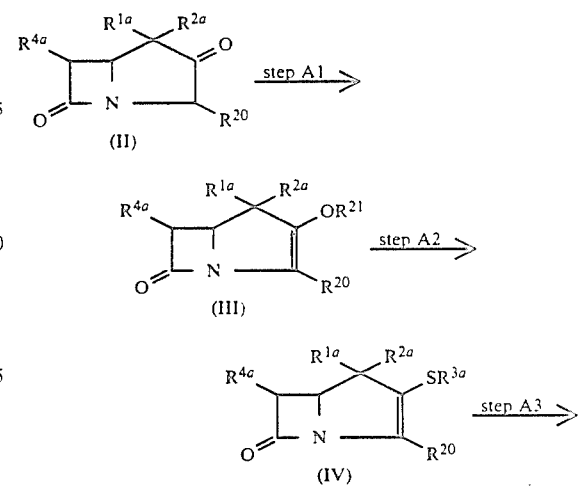

In the above formulae, $R^1$, $R^2$, $R^3$, $R^4$, $R^{1a}$, $R^{2a}$, $R^{3a}$, $R^{4a}$, $R^{20}$ and $R^{21}$ are as defined above.

$R^{4a}$ represents any one of the groups or atoms represented by $R^4$ or any such group in which any active group is protected. In particular, $R^{4a}$ preferably represents a hydrogen atom, a $C_1$-$C_6$ alkyl group or a group of formula $R^{30}A$— (in which $R^{30}$ represents a hydroxy group, an alkoxy group, an acyloxy group, an alkylsulfonyloxy group, an arylsulfonyloxy group, a trialkylsilyloxy group, an acylthio group, an alkylthio group, an acylamino group or an aralkylamino group; and A represents a $C_1$-$C_6$ alkylene group optionally having a trifluoromethyl or phenyl substituent).

Where any of the substituents on the compound of formula (II) is or includes a hydroxy, mercapto, amino or carboxy group, such groups may be left unprotected, but are preferably protected prior to carrying out any other reactions; such protection has no significance in the overall reaction scheme, in that protecting groups are normally removed at the end of the reaction sequence, but does have the substantial practical advantage that it improves overall yields by reducing the possibility of side-reactions. Accordingly, the nature of the protecting groups employed is in no way critical to the present invention and a very wide range of protecting groups may be used, the nature of such protecting groups being dependent on the nature of the group which it is intended to protect. Such protecting groups are extremely well-known to those skilled in this art and require no specific definition here. However, examples of suitable protecting groups are discussed hereafter in relation to step A3, where the protecting groups are removed.

In step A1 of this reaction scheme, the compound of formula (II) is reacted with a compound of formula (IIa):

  (IIa)

(in which $R^{21}$ is as defined above). $R^{21}$ is preferably a $C_1$–$C_6$ alkanesulfonyl group, a benzenesulfonyl, naphthalenesulfonyl or p-toluenesulfonyl group, a dialkylphosphoryl group in which each alkyl part has from 1 to 6 carbon atoms or a diarylphosphoryl group in which each aryl part is a $C_6$–$C_{10}$ carbocyclic aryl group, preferably phenyl or naphthyl. However, the nature of the group represented by $R^{21}$ is of no overall significance in the process of the invention, in that this group is removed in the course of the reactions and plays no part in the final product.

Instead of using the compound of formula (IIa) as such, it is possible to employ an active derivative of such a compound. Suitable active derivatives include anhydrides and halides, particularly chlorides. In particular, we prefer to employ an anhydrous alkanesulfonic acid, an anhydrous arylsulfonic acid, a dialkylphosphoryl halide or a diarylphosphoryl halide. Preferred alkanesulfonic acids include methanesulfonic acid and ethanesulfonic acid. Preferred arylsulfonic acids include benzenesulfonic acid and p-toluenesulfonic acid. Preferred dialkylphosphoryl halides include dimethylphosphoryl chloride and diethylphosphoryl chloride. Preferred diarylphosphoryl halides include diphenylphosphoryl chloride and diphenylphosphoryl bromide. In particular, we prefer to employ anhydrous p-toluenesulfonic acid or diphenylphosphoryl chloride.

The reaction is preferably effected in the presence of a base, the nature of which is not critical, provided that it has no adverse effect on the reaction or upon the reagents, in particular the β-lactam ring. Preferred bases are organic bases, particularly triethylamine, diisopropylethylamine and 4-dimethylaminopyridine.

The reaction is preferably effected in the presence of a solvent, the nature of which is likewise not critical, provided that it has no adverse effect upon the reaction. Suitable solvents include: halogenated hydrocarbons, such as methylene chloride, 1,2-dichloroethane and chloroform; nitriles, such as acetonitrile; and amides, such as dimethylformamide or dimethylacetamide.

The reaction may be carried out over a wide range of temperatures, the reaction temperature not being critical, but we prefer to employ a relatively low temperature, in order to reduce or control side reactions. Accordingly, we prefer to employ a temperature of from −20° C. to 40° C. The time required for the reaction will vary depending upon many factors, but particularly on the reaction temperature and the nature of the reagents; however, a period of from 10 minutes to 5 hours will normally suffice.

The resulting compound of formula (III) is then reacted in step A2 with a mercaptan of formula (IIIa):

  (IIIa)

(in which $R^{3a}$ is as defined above), preferably without intermediate isolation of the compound of formula (III). This reaction, like the reaction in step A1, is preferably effected in the presence of a base, the nature of which is not critical, provided that it does not adversely affect the reaction or adversely affect the reagents, particularly the β-lactam ring. Suitable bases include: organic amines, such as triethylamine or diisopropylethylamine; and inorganic bases, particularly alkali metal carbonates, such as sodium carbonate or potassium carbonate.

The reaction temperature is not critical, but, in order to reduce or control side reactions, a relatively low temperature is preferably employed. A suitable temperature is from −20° C. to room temperature. The time required for the reaction will vary depending upon many factors, but primarily upon the reaction temperature and the nature of the reagents. However, a period of from 30 minutes to 8 hours will normally suffice.

After completion of the above reactions, the resulting product of formula (IV) may, if desired, be recovered from the reaction mixture by conventional means. For example, one suitable recovery procedure comprises: distilling the reaction solvent from the reaction mixture; adding a water-immiscible organic solvent to the residue; washing the mixture with water and, if necessary, drying it; and distilling off the solvent to give the desired product. If necessary, the resulting product may be further purified by a variety of conventional means adapted to the precise nature of the product; suitable further purification techniques include recrystallization, reprecipitation and the various chromatographic techniques, for example column chromatography or preparative thin layer chromatography.

Step A3 of the reaction scheme is optional and involves a variety of possible reactions, any one or more of which may be employed, in any suitable order, if desired.

Thus, if the compound of formula (IV) obtained as described above contains a carboxy-protecting group, for example if the group represented by $R^{20}$ is a protected carboxy group, the carboxy-protecting group may be removed to leave a free carboxy group; the reactions employed to do this are conventional and depend upon the nature of the protecting group.

If the protecting group is removable by reduction, for example if it is a haloalkyl group, an aralkyl group or a benzhydryl group, it may be removed by contact with a reducing agent. In the case of haloalkyl groups, such as the 2,2-dibromoethyl or 2,2,2-trichloroethyl groups, the preferred reducing agent is a combination of zinc with acetic acid. If the protecting group is an aralkyl group (such as a benzyl or p-nitrobenzyl group) or a benzhydryl group, we prefer that the reduction should be either: catalytic reduction using hydrogen and a suitable catalyst, such as platinum- or palladium-on-charcoal; or reduction with an alkali metal sulfide, such as sodium sulfide or potassium sulfide. Whatever the reduction technique, the reduction process is preferably effected in the presence of a solvent, the nature of which is not critical, provided that it has no adverse effect upon the reaction. Suitable solvents include: alcohols, such as methanol or ethanol; ethers, such as tetrahydrofuran or dioxane; fatty acids, such as acetic acid; or a mixture of one or more of these organic solvents with water. The reaction may be carried out over a wide temperature range, although we generally find it convenient to carry out the reaction at a temperature in the range from 0° C. to room temperature. The time required for the reaction will vary, depending upon the nature of the starting materials and reducing agents, as well as upon the reaction temperature, but a period of from 5 minutes to 12 hours will normally suffice.

After completion of the reaction, the desired compound, which will contain a free carboxy group, may be recovered by conventional means from the reaction mixture. For example, a suitable recovery technique comprises: separating off any insolubles; washing the organic solvent layer with water and, if necessary, drying it; and then distilling off the solvent to give the desired product. This may, if necessary, be further purified by conventional means, for example recrystallization or the various chromatography techniques, such as preparative thin layer chromatography or column chromatography.

If the group represented by $R^{4a}$ in the compound of formula (IV) contains an acyloxy group, a trialkylsilyloxy group, an acylamino group or an aralkylamino group, the protecting groups may, if desired, be removed by conventional means, as described below, to restore a hydroxy group or an amino group. Removal of these hydroxy-protecting or amino-protecting groups may be carried out prior to, simultaneously with or after removal of any carboxy-protecting group in a protected carboxy group represented by $R^{20}$.

For example, if the protecting group, for example any such group in the group represented by $R^{4a}$, is a lower (e.g. $C_1-C_7$) aliphatic acyloxy group, such as an acetoxy group, this may be removed by treating the corresponding compound with a base in the presence of an aqueous solvent. The nature of the solvent is not critical and any such solvent commonly used for hydrolysis reactions may be employed. However, we normally prefer to use water or a mixture of water with an organic solvent, such as an alcohol (e.g. methanol, ethanol or propanol) or an ether (e.g. tetrahydrofuran or dioxane). The nature of the base is also not critical to the process, provided that it does not adversely affect any other part of the compound, notably the $\beta$-lactam ring; preferred bases are alkali metal carbonates, such as sodium carbonate or potassium carbonate. The reaction temperature is not critical, but we normally prefer to employ a temperature of from 0° C. to about room temperature, in order to reduce or control side reactions. The time required for the reaction will vary, depending upon many factors, including the nature of the starting materials and the reaction temperature, but a period of from 1 to 6 hours will normally suffice.

If the hydroxy-protecting group is an aralkyloxycarbonyl group (such as a benzyloxycarbonyl or p-nitrobenzyloxycarbonyl group), this may be eliminated to restore a free hydroxy group by contacting the compound with a reducing agent. The nature of the reducing agent and the reaction conditions are precisely the same as those employed for removing a carboxy-protecting group where this carboxy-protecting group is an aralkyl group; accordingly, if the compound contains both an aralkyloxycarbonyl group (as hydroxy-protecting group) and an aralkyl group (as carboxy-protecting group), these will be removed simultaneously. Similarly, the same reaction can be employed to remove amino-protecting groups, where these are aralkyloxycarbonyl groups (such as benzyloxycarbonyl or p-nitrobenzyloxycarbonyl groups), aralkyl groups or benzhydryl groups, to restore a free amino group.

Where the compound contains a trialkylsilyloxy group in which each alkyl group has from 1 to 6 carbon atoms (for example a t-butyldimethylsilyloxy group) as a protected hydroxy group, the protecting group may be eliminated by treating the compound with tetrabutylammonium fluoride. The reaction is preferably effected in the presence of a solvent, the nature of which is not critical, provided that it has no adverse effect upon the reaction; suitable solvents include ethers such as tetrahydrofuran or dioxane. The reaction is preferably effected at about room temperature and the period required for the reaction, which will vary depending upon the reagents and reaction temperature, will normally be from 10 to 18 hours.

If the compound of formula (IV) contains a haloacetyl group (such as a trifluoroacetyl or trichloroacetyl group) as a hydroxy-protecting or amino-protecting group, this may be eliminated by treating the compound with a base in the presence of an aqueous solvent. The nature of the bases and the reaction conditions are the same as are employed for removal of lower aliphatic acyl groups when employed as hydroxy-protecting groups in the group represented by $R^{4a}$.

Also at this stage, where $R^3$ in the resulting compound of formula (I) or $R^{3a}$ in the compound (IV) represents a heterocyclic group having a ring nitrogen atom attached to a hydrogen atom, this hydrogen atom may be replaced by an imidoyl group of formula:

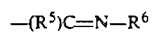

(in which $R^5$ and $R^6$ are as defined above). This may be achieved by reacting the corresponding compound of formula (I) or (IV) with an imidoester of formula (XV):

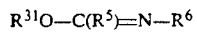

(in which $R^5$ and $R^6$ are as defined above and $R^{31}$ represents a $C_1-C_6$ alkyl group, preferably a methyl, ethyl, propyl or isopropyl group).

The reaction is preferably effected in the presence of a solvent, the nature of which is not critical, provided that it has no adverse effect upon the reaction. A suitable solvent is an aqueous phosphate buffer solution whose composition is such as to maintain a pH value of about 8. Although the reaction will take place over a wide range of temperatures, in order to reduce or control side reactions, we prefer to employ a relatively low temperature, for example a temperature of from 0° C. to about room temperature. The time required for the reaction will vary, depending upon many factors, including the nature of the reagents and the reaction temperature, but a period of from 10 minutes to 2 hours will normally suffice.

After completion of this reaction, the desired product may be recovered from the reaction mixture by conventional means and, if necessary, further purified by such conventional techniques as recrystallization, preparative thin layer chromatography and column chromatography.

Where the compound of formula (IV) or (I) obtained as described above contains a heterocyclic group having a ring nitrogen atom attached to a hydrogen atom, this hydrogen atom may be replaced by an acyl group by reacting the compound of formula (IV) or (I) with a carboxylic acid corresponding to the acyl group which it is desired to introduce or with an active derivative of such a carboxylic acid, for example the acid halide, acid anhydride or active ester. Suitable acid halides include acid chlorides (such as acetyl chloride or propionyl chloride). Suitable acid anhydrides include carboxylic acid anhydrides (such as acetic anhydride) or mixed acid anhydrides (for example those of a carboxylic acid with ethyl chloroformate). Suitable active esters include, for example, the p-nitrobenzyl ester, the 2,4,5-trichlorophenyl ester, the cyanomethyl ester, the N-phthaloylimido ester and the N-hydroxysuccinimido ester of the carboxylic acid.

If the carboxylic acid itself is employed, we prefer that the reaction should be carried out in the presence of a dehydrating agent (such as dicyclohexylcarbodiimide or carbonyldiimidazole) or of a Vilsmeyer reagent (prepared from dimethylformamide and phosphorous oxychloride or thionyl chloride).

The reaction between the compound of formula (IV) or (I) and one of the above-mentioned acylating agents is preferably effected either in a suitable buffer solution (for example a phosphate buffer solution formulated to maintain a pH value of from 8.0 to 8.5) or in the presence of an inert organic solvent and a base. Where an organic solvent is employed, the nature of the solvent is not critical, provided that it has no adverse effect upon the reaction. Suitable solvents include: halogenated hydrocarbons, such as methylene chloride, 1,2-dichloroethane or chloroform; nitriles, such as acetonitrile; ethers, such as diethyl ether, tetrahydrofuran or dioxane; and amides, such as dimethylformamide or dimethylacetamide. The nature of the base is likewise not critical, provided that it does not have any adverse effect upon other parts of the molecule and most notably on the β-lactam ring; organic bases are preferred, for example triethylamine, diisopropylethylamine, pyridine or 2,6-lutidine.

The reaction may be carried out over a wide range of temperatures and hence the reaction temperature is not critical; however, in order to reduce or control side reactions, a relatively low temperature is preferred, for example a temperature from −20° C. to about room temperature. The time required for the reaction will vary, depending upon many factors, but particularly on the reaction temperature and the nature of the reagents; however, a period of from 10 minutes to 5 hours will normally suffice.

After completion of the reactions described above, the desired product may be recovered from the reaction mixture by conventional means. For example, when the reaction is carried out in a buffer solution, the desired product is preferably separated by column chromatography, for example through a column of Diaion (trade mark) HP-20AG (a product of Mitsubishi Chemical Industries Co Ltd). On the other hand, if the compound is obtained by reaction in an organic solvent, the solution is washed with water (if necessary, after transferring the product into solution in a water-immiscible organic solvent), the solution is, if necessary, dried, and then the solvent is distilled off to give the desired product. This product may, if necessary, be further purified by conventional techniques, for example by recrystallization, reprecipitation or the various chromatography techniques, such as preparative thin layer chromatography or column chromatography.

METHOD B

Compounds of formula (I) in which $R^3$ represents a tetrahydropyrimidinyl or similar group, that is to say compounds of formula (Ia) may be prepared as illustrated in the following reaction scheme:

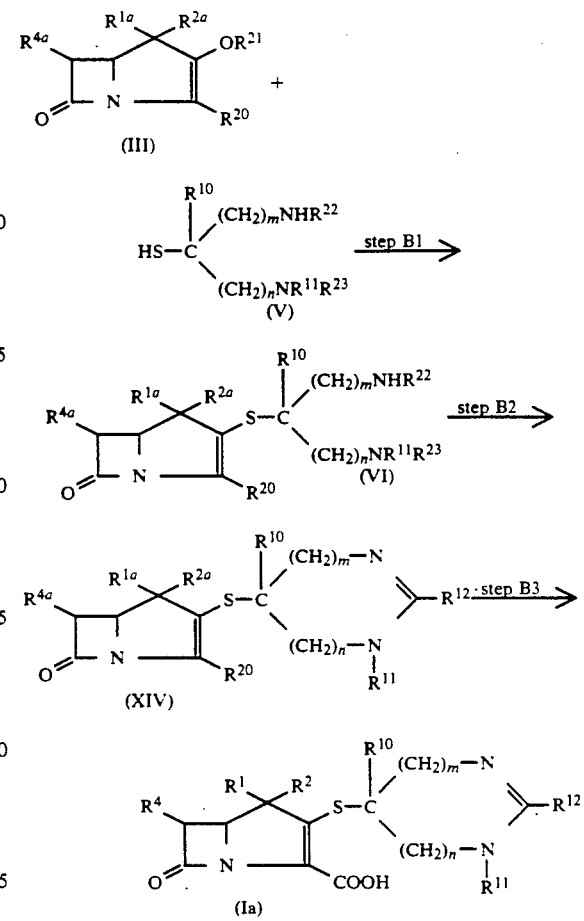

In the above formulae, $R^1$, $R^2$, $R^4$, $R^{1a}$, $R^{2a}$, $R^{4a}$, $R^{10}$, $R^{11}$, $R^{12}$, $R^{20}$, $R^{21}$, $R^{22}$, $R^{23}$, m and n are as defined above. Examples of amino-protecting groups which may be represented by $R^{22}$ and $R^{23}$ include the aralkyloxycarbonyl groups (e.g. the benzyloxycarbonyl or p-nitrobenzyloxycarbonyl groups), the benzhydryloxycarbonyl group, aryloxycarbonyl groups, aralkyl groups, the benzhydryl group and haloacetyl groups (such as the trifluoroacetyl or trichloroacetyl groups).

The compound of formula (III), shown as the starting material in this reaction scheme, may be, and preferably is, prepared as described in step A1 of Method A.

In step B1 of this reaction, the compound of formula (III) and the mercaptan of formula (V) are reacted together to give the compound of formula (VI). This reaction is precisely the same as the reaction employed in step A2 of Method A and may be carried out using the same solvents and under the same conditions.

Step B2 of this reaction scheme comprises first eliminating the amino-protecting groups represented by $R^{22}$ and $R^{23}$ and then reacting the resulting diamino compound with an imino ether to give the compound of formula (XIV).

Removal of the amino-protecting groups may be carried out by conventional means: the precise nature of the reaction depending upon the nature of the protecting group. For example, where the protecting group is an aralkyloxycarbonyl group (e.g. benzyloxycarbonyl or p-nitrobenzyloxycarbonyl), it may be removed by catalytic reduction, using hydrogen and a catalyst, such as platinum or palladium-on-charcoal; under these conditions, hydroxy-protecting groups, amino-protecting groups or carboxy-protecting groups in the groups represented by $R^{4a}$, $R^{1a}$, $R^{2a}$, and $R^{20}$ may occasionally also be eliminated. The product of this reaction is preferably then reacted with an imino ether of formula (VIa):

$$R^{24}O-C(R^{12})=NH \qquad (VIa)$$

(in which $R^{12}$ and $R^{24}$ are as defined above), preferably without intermediate isolation. The reaction is preferably effected in the presence of a suitable solvent, for example a phosphate buffer solution having a composition such as to maintain a pH value of about 8.0. The reaction is preferably effected at relatively low temperature, for example from 0° C. to about room temperature and the time required for this reaction will normally vary from 10 minutes to 2 hours.

After completion of the reaction, the desired product of formula (XIV) may be recovered from the reaction mixture by conventional means and, if necessary, further purified by such conventional techniques as recrystallization, preparative thin layer chromatography or column chromatography.

In step B3, which is an optional step, protecting groups may be removed and other reactions may be carried out, as illustrated in relation to the corresponding reaction in step A3.

METHOD C

As an alternative to Methods A and B, compounds of the invention may be prepared by the method illustrated by the following reaction scheme.

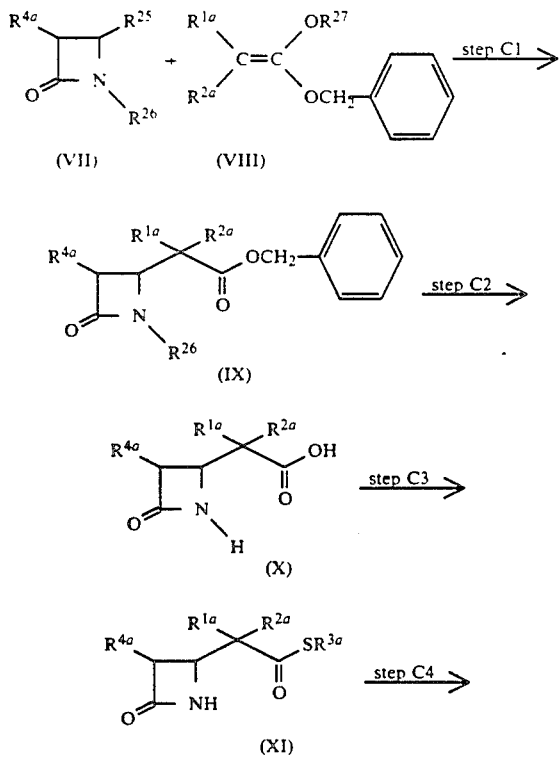

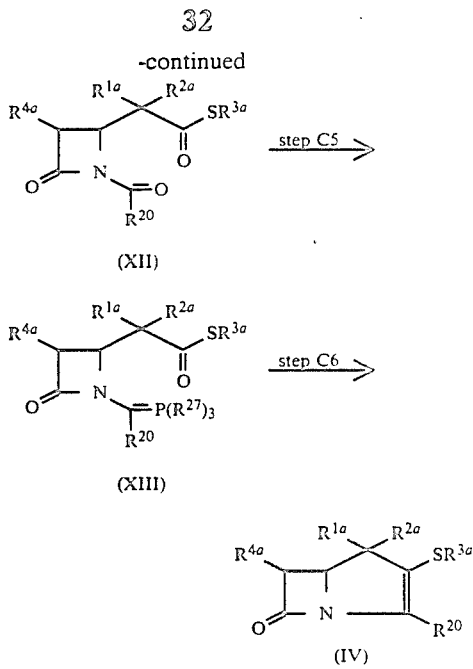

In the above formulae, $R^{1a}$, $R^{2a}$, $R^{3a}$, $R^{4a}$, $R^{20}$, $R^{25}$, $R^{26}$ and $R^{27}$ are as defined above.

In step C1 of this reaction scheme, the compound of formula (VII) is reacted with a compound of formula (VIII), to give a compound of formula (IX). This compound of formula (IX) is reacted in step C2 first with water and then with hydrogen in the presence of a catalyst, for example palladium-on-charcoal, to give the compound of formula (X). If any of the groups represented by $R^{1a}$, $R^{2a}$ or $R^{4a}$ contains a protecting group removable by reduction, then this may be removed during this step.

In step C3, the compound of formula (X) is reacted with a mercaptan of formula $R^{3a}SH$, to give the compound of formula (XI). This reaction is precisely the same as the corresponding reaction in step A2 and may be carried out using the same reagents and under the same conditions.

The compound of formula (XI) is then reacted in step C4 with an oxalyl halide derivative of formula (XIa):

$$R^{20}.CO.Hal \qquad (XIa)$$

to give the compound of formula (XII).

This compound of formula (XII) is reacted, in step C5, with a phosphorus compound of formula $P(R^{27})_3$. Particularly preferred phosphorus compounds are the trialkyl phosphites, of which triethyl phosphite, tripropyl phosphite and triisopropyl phosphite are the most preferred. This reaction is preferably effected in the presence of an inert solvent, for example: an aliphatic or aromatic hydrocarbon, such as hexane, benzene, toluene or xylene; a halogenated hydrocarbon, such as chloroform, methylene chloride or 1,2-dichloroethane; an ester, such as ethyl acetate; an ether, such as tetrahydrofuran or dioxane; a nitrile, such as acetonitrile; or an amide, such as dimethylformamide.

The reaction of step C5 is preferably effected with heating, for example at a temperature within the range from 50° to 150° C. The time required for the reaction will vary depending upon many factors, including the nature of the reagents and the reaction temperature, but a period of from 1 to 10 hours will normally suffice. At the end of this time, the solvent and other substances are distilled off under reduced pressure, giving the compound of formula (XIII). Depending upon the reaction temperature and the time allowed for the reaction, the compound of formula (XIII) may already have undergone cyclization to convert some or all of that compound into the compound of formula (IV). Thus, if the reaction in step C5 was carried out at a temperature within the range of from 80° to 150° C. for a period of from 10 hours to 5 days, without isolation of the compound of formula (XIII), the compound (IV) is obtained directly. If, however, the compound has not undergone cyclization, then it is preferably heated, e.g. at a temperature within the range from 80° to 150° C. for a period of from 10 hours to 5 days, to give the desired compound of formula (IV) as step C6.

If desired, the resulting compound of formula (IV) may be subjected to any of the reactions heretofore described in step A3 of Method A to give the compound of formula (I) or a salt or ester thereof.

The compounds obtained by any of the above Methods may, if desired, be salified and/or esterified by conventional means, to give salts and/or esters thereof, examples of such salts and esters being given previously.

Some of the compounds of formula (I) have, in themselves, outstanding antibacterial activity, whilst others, although generally exhibiting some antibacterial activity, are of more value as intermediates for the preparation of other compounds having good antibacterial activity. Those compounds having antibacterial activity exhibit this effect against a wide range of pathogenic microorganisms, including both gram-positive bacteria (such as *Staphylococcus aureus* and *Bacillus subtilis*) and gram-negative bacteria (such as *Escherichia coli, Shigella flexneri, Klebsiella pneumoniae, Proteus vulgaris,* Serratia species e.g. *Serratia marcescens,* Enterobacter species e.g. *Enterobacter cloacae, Salmonella enteritidis* and *pseudomonas aeruginosa*) and are thus useful for the treatment of diseases caused by such microorganisms.

Certain of the compounds of the invention were investigated for their activities against various microorganisms. The compounds tested were:

A: (5R)-6(S)-[1(R)-hydroxyethyl]-1(R)-methyl-2-[(3S)-pyrrolidin-3-ylthio]carbapen-2-em-3-carboxylic acid;

B: (5R)-2-[(3R)-1-acetimidoylpyrrolidin-3-ylthio]-6(S)-[1(R)-hydroxyethyl]-1(R)-methylcarbapen-2-em-3-carboxylic acid;

C: (5R)-2-[(3S)-5(S)-carbamoylpyrrolidin-3-ylthio]-6(S)-[1(R)-hydroxyethyl]-1(R)-methylcarbapen-2-em-3-carboxylic acid; and D: thienamycin.

The activities of the test compounds of the invention, identified by the letters assigned to them above, against various bacteria are shown in the following Table, in terms of their minimal inhibitory concentrations (μg/ml).

| Microorganism | Compound No. | | | |
|---|---|---|---|---|
| | A | B | C | D |
| Staphylococcus aureus 209P | ≦0.01 | ≦0.01 | ≦0.01 | ≦0.01 |
| Staphylococcus aureus 56 | ≦0.01 | ≦0.01 | 0.02 | ≦0.01 |
| Escherichia coli NIHJ | ≦0.01 | ≦0.01 | ≦0.01 | 0.1 |
| Escherichia coli 609 | ≦0.01 | ≦0.01 | ≦0.01 | 0.1 |

-continued

| Microorganism | Compound No. | | | |
|---|---|---|---|---|
| | A | B | C | D |
| Shigella flexneri 2a | ≦0.01 | 0.02 | ≦0.01 | 0.1 |
| Pseudomonas aeruginosa | 0.8 | 6.2 | 0.8 | 6.2 |
| Klebsiella pneumoniae 806 | ≦0.01 | ≦0.01 | ≦0.01 | 0.1 |
| Klebsiella pneumoniae 846 | ≦0.01 | ≦0.01 | ≦0.01 | 0.1 |
| Proteus vulgaris | 0.4 | 0.2 | 0.05 | 3.1 |
| Salmonella enteritidis G. | 0.02 | ≦0.01 | ≦0.01 | 0.2 |
| Serratia marcescens | 0.02 | 0.02 | ≦0.01 | — |
| Enterobacter cloacae | 0.2 | 0.2 | 0.1 | — |

As can be seen from the above Table, the activities of the compounds of the invention, in the in vitro test, are comparable with or better than the activities of the known compound, thienamycin and are also generally better than the compounds of U.S. Ser. No. 407,914. However, as already noted, the compounds of the invention show much greater stability in the body than does thienamycin and thus the compounds of the invention exhibit much better activities than thienamycin when tested in vivo.

It is well known in the art that compounds having a low minimal inhibitory concentration, and which are, as a result, expected to be valuable in chemotherapy, sometimes fail to show a good antibacterial effect when they are administered to humans or other animals. This may be due to various causes, for example chemical or physiological instability of the compounds, poor distribution of the compounds in the body or binding of the compounds to blood serum. The compounds of the invention, however, do not seem to exhibit such problems and thus are expected to show a remarkable in vivo activity.

The compounds of the invention may be administered either orally or parenterally for the treatment of diseases in humans and other animals caused by pathogenic microorganisms. The compounds may be formulated into any conventional forms for administration. For example, for oral administration, suitable formulations include tablets, granules, capsules, powders and syrups, whilst formulations for parenteral administration include injectable solutions for intramuscular or, more preferably intravenous, injection.

The compounds of the invention are preferably administered parenterally, particularly in the form of an intravenous injection.

The dose of the compound of the invention will vary, depending upon the age, body weight and condition of the patient, as well as upon the form and times of administration. However, in general the adult daily dose is from 200 to 3000 mg of the compound, which may be administered in a single dose or in divided doses.

The preparation of compounds of the invention is further illustrated by the following Examples.

EXAMPLE 1 p-Nitrobenzyl
(1S,5R,6S)-6-[1(R)-hydroxyethyl]-1-methyl-2-[(3R)-1-(N-p-nitrobenzyloxycarbonylacetimidoyl)pyrrolidin-3-ylthio]carbapen-2-em-3-carboxylate (Compound No. 115)

0.174 ml of diisopropyl(ethyl)amine and 0.245 ml of diphenylphosphoryl chloride were added, under a nitrogen atmosphere and with ice-cooling, to 5 ml of an acetonitrile solution containing 363 mg of p-nitrobenzyl (1S,5R,6S)-6-[1(R)-hydroxyethyl]-1-methyl-2-oxocarbapenam-3-carboxylate. The mixture was stirred for 2 hours at the same temperature, and then a further 0.2 ml of diisopropyl(ethyl)amine and 330 mg of 3(R)-mercapto-1-(N-p-nitrobenzyloxycarbonylacetimidoyl)pyrrolidine were added to the mixture, which was then stirred for one hour. The reaction mixture was then diluted with ethyl acetate, washed with water and with a saturated aqueous solution of sodium chloride and dried over anhydrous magnesium sulfate. The solvent was then distilled off. The resulting residue was then subjected to chromatography through a short column packed with silica gel to remove impurities, giving 450 mg of the title compound as an oily substance which had partly crystallized.

Nuclear Magnetic Resonance Spectrum
(60 MHz, CDCl$_3$+sufficient CD$_3$OD to dissolve the test compound) δ ppm:
1.3 (3H, doublet);
1.4 (3H, doublet);
1.8–2.4 (3H, multiplet);
2.3 (3H, singlet);
3.0–4.3 (8H, multiplet);
5.15 (2H, singlet);
5.32 (2H, AB);
7.3, 8.1 (A$_2$B$_2$);
7.5, 8.1 (A$_2$B$_2$).

EXAMPLE 2

(1S,5R,6S)-2-[(3R)-1-acetimidoylpyrrolidin-3-ylthio]-6-[1(R)-hydroxyethyl]-1-methylcarbapen-2-em-3-carboxylic acid (Compound No. 23)

80 ml of water and 1.6 g of 10% w/w palladium-on-carbon were added to 50 ml of a tetrahydrofuran solution containing 450 mg of p-nitrobenzyl (1S,5R,6S)-6-[1(R)-hydroxyethyl]-1-methyl-2-[(3R)-1-(N-p-nitrobenzyloxycarbonylacetimidoyl)pyrrolidin-3-ylthio]carbapen-2-em-3-carboxylate (obtained as described in Example 1) and the mixture was stirred for 2 hours in a hydrogen atmosphere. The catalyst was filtered off, the tetrahydrofuran was distilled off under reduced pressure and the residue was washed with ethyl acetate. The aqueous layer was condensed by evaporation under reduced pressure to a volume of approximately 50 ml, and then subjected to column chromatography using Diaion CHP-20P (a trade name for a product of Mitsubishi Chemical Industries). 62 mg of the desired compound were obtained from the fraction eluted with 5% v/v aqueous acetone.

Nuclear Magnetic Resonance Spectrum (90 MHz, D$_2$O) δ ppm:
1.02 (3H, doublet);
1.06 (3H, doublet);
2.03 (3H, singlet);
1.8–2.3 (2H, multiplet);
3.0–4.2 (9H, multiplet).
Infrared Absorption Spectrum (KBr) $\nu_{max}$ cm$^{-1}$:
3400, 1760, 1675.

EXAMPLE 3 p-Nitrobenzyl
(1S,5R,6S)-6-[1(R)-hydroxyethyl]-1-methyl-2-[(3S)-1-(N-p-nitrobenzyloxycarbonylacetimidoyl)pyrrolidin-3-ylthio]carbapen-2-em-3-carboxylate (Compound No. 115)

The procedure described in Example 1 was repeated, but using 365 mg of p-nitrobenzyl (1S,5R,6S)-6-[1(R)-hydroxyethyl]-1-methyl-2-oxocarbapenam-3-carboxylate and 390 mg of 3(S)-mercapto-1-(N-p-nitrobenzyloxycarbonylacetimidoyl)pyrrolidine, to give 360 mg of the title compound.

Nuclear Magnetic Resonance Spectrum (60 MHz, CDCl$_3$) δ ppm:
1.3 (3H, doublet);
1.4 (3H, doublet);
2.29 (3H, singlet);
1.6–2.5 (3H, multiplet);
2.9–4.5 (8H, multiplet);
5.21 (2H, singlet);
5.28, 5.44 (2H, AB);
7.59, 8.20 (4H, A$_2$B$_2$);
7.67, 8.24 (4H, A$_2$B$_2$).

EXAMPLE 4

(1S,5R,6S)-2-[(3S)-1-Acetimidoylpyrrolidin-3-ylthio]-6-[1(R)-hydroxyethyl]-1-methylcarbapen-2-em-3-carboxylic acid (Compound No. 23)

The catalytic hydrogenation process described in Example 2 was repeated, but using 360 mg of p-nitrobenzyl (1S,5R,6S)-6-[1(R)-hydroxyethyl]-1-methyl-2-[(3S)-1-(N-p-nitrobenzyloxycarbonylacetimidoyl)pyrrolidin-3-ylthio]carbapen-2-em-3-carboxylate (obtained as described in Example 3), to give 60 mg of the title compound.

Nuclear Magnetic Resonance Spectrum (400 MHz, D$_2$O) δ ppm:
1.09 (3H, doublet, J=6.4 Hz);
1.16 (3H, doublet, J=6.8 Hz);
1.7–2.0 (1H, multiplet);
2.07, 2.08 (each 1.5H, singlet);
2.1–2.3 (1H, multiplet);
3.1–3.95 (8H, multiplet);
4.0–4.2 (1H, multiplet).
Ultraviolet Absorption Spectrum (H$_2$O) $\lambda_{max}$ nm(ε):
289 (4790).
Infrared Absorption Spectrum (KBr) $\nu_{max}$ cm$^{-1}$:
3400, 1760, 1675.

EXAMPLE 5 p-Nitrobenzyl
(1R,5R,6S)-6-[1(R)-hydroxyethyl]-1-methyl-2-[(3R)-1-(N-p-nitrobenzyloxycarbonylacetimidoyl)pyrrolidin-3-ylthio]carbapen-2-em-3-carboxylate (Compound No. 115)

The procedure described in Example 1 was repeated, but using 363 mg of p-nitrobenzyl (1R,5R,6S)-6-[1(R)-hydroxyethyl]-1 methyl-2-oxocarbapenam-3-carboxylate and 430 mg of 3(R)-mercapto-1-(N-p-nitrobenzyloxycarbonylacetimidoyl)pyrrolidine, to give 430 mg of the title compound.

Nuclear Magnetic Resonance Spectrum (60 MHz, CDCl$_3$ + sufficient CD$_3$OD to dissolve the compound) δ ppm:
- 1.3 (3H, doublet);
- 1.4 (3H, doublet);
- 1.8–2.4 (3H, multiplet);
- 2.3 (3H, singlet);
- 3.0–4.3 (8H, multiplet);
- 5.20 (2H, singlet);
- 5.35 (2H, AB);
- 7.5, 8.2 (4H, A$_2$B$_2$);
- 7.6, 8.2 (4H, A$_2$B$_2$).

EXAMPLE 6

(1R,5R,6S)-2-[(3R)-1-Acetimidoylpyrrolidin-3-ylthio]-6-[1(R)-hydroxyethyl]-1-methylcarbapen-2-em-3-carboxylic acid (Compound No. 23)

The catalytic hydrogenation process described in Example 2 was repeated, but using 430 mg of p-nitrobenzyl (1R,5R,6S)-6-[1(R)-hydroxyethyl]-1-methyl-2-[(3R)-1-(N-p-nitrobenzyloxycarbonylacetimidoyl)pyrrolidin-3-ylthio]carbapen-2-em-3-carboxylate (prepared as described in Example 5), to give 110 mg of the title compound.

Nuclear Magnetic Resonance Spectrum (400 MHz, D$_2$O) δ ppm:
- 1.04 (3H, doublet, J=6.8 Hz);
- 1.10 (3H, doublet, J=6.4 Hz);
- 1.85–2.05 (1H, multiplet);
- 2.08 (1.5H, singlet);
- 2.09 (1.5H, singlet);
- 2.2–2.35 (1H, multiplet);
- 3.2–3.75 (6H, multiplet);
- 3.8–3.95 (1H, multiplet);
- 4.0–4.25 (2H, multiplet).

Ultraviolet Absorption Spectrum (H$_2$O) ν$_{max}$ nm(ε): 298 (7960).

Infrared Absorption Spectrum (KBr) ν$_{max}$ cm$^{-1}$: 3400, 1760, 1675.

EXAMPLE 7 p-Nitrobenzyl (1R,5R,6S)-6-[1(R)-hydroxyethyl]-1-methyl-2-[(3S)-1-(p-nitrobenzyloxycarbonyl)pyrrolidin-3-ylthio]carbapen-2-em-3-carboxylate (Compound No. 116)

The process described in Example 1 was repeated, but using 1.35 g of p-nitrobenzyl (1R,5R,6S)-6-[1(R)-hydroxyethyl]-2-oxocarbapenam-3-carboxylate and 1.43 g of 3(S)-mercapto-1-(p-nitrobenzyloxycarbonyl)pyrrolidine, to give 1.8 g of the title compound.

Nuclear Magnetic Resonance Spectrum (CDCl$_3$) δ ppm:
- 1.30 (3H, doublet, J=6 Hz);
- 1.38 (3H, doublet, J=6 Hz);
- 1.6–2.5 (2H, multiplet);
- 3.1–4.4 (10H, multiplet);
- 5.17 (1H, doublet, J=15 Hz);
- 5.20 (2H, singlet);
- 5.52 (1H, doublet, J=15 Hz);
- 7.47 (2H, doublet, J=9 Hz);
- 7.62 (2H, doublet, J=9 Hz);
- 8.20 (4H, doublet, J=9 Hz).

Infrared Absorption Spectrum (KBr) ν$_{max}$ cm$^{-1}$: 3400, 1770, 1705.

EXAMPLE 8

(1R,5R,6S)-6-[1(R)-Hydroxyethyl]-1-methyl-2-[(3S)-pyrrolidin-3-ylthio]carbapen-2-em-3-carboxylic acid (Compound No. 14)

The catalytic hydrogenation process described in Example 2 was repeated, but using 0.8 g of p-nitrobenzyl (1R,5R,6S)-6-[1(R)-hydroxyethyl]-1-methyl-2-[(3S)-1-(p-nitrobenzyloxycarbonyl)pyrrolidin-3-ylthio)]carbapen-2-em-3-carboxylate (prepared as described in Example 7), to give 0.25 g of the title compound.

Nuclear Magnetic Resonance Spectrum (D$_2$O) δ ppm:
- 1.03 (3H, doublet, J=7 Hz);
- 1.10 (3H, doublet, J=6 Hz);
- 1.7–1.9 (1H, multiplet);
- 2.2–2.4 (1H, multiplet);
- 3.0–4.1 (9H, multiplet).

Infrared Absorption Spectrum (KBr) ν$_{max}$ cm$^{-1}$: 3400, 1760, 1590.

Ultraviolet Absorption Spectrum (H$_2$O) λ$_{max}$ nm(ε): 296.8 (8460).

EXAMPLE 9

(1R,5R,6S)-2-[(3S)-1-Acetimidoylpyrrolidin-3-ylthio]-6-[1(R)-hydroxyethyl]-1-methylcarbapen-2-em-3-carboxylic acid (Compound No. 23)

100 mg of (1R,5R,6S)-6-[1(R)-hydroxyethyl]-1-methyl-2-[(3S)-pyrrolidin-3-ylthio]carbapen-2-em-3-carboxylic acid (prepared as described in Example 8) were dissolved in 1.2 ml of a phosphate buffer (pH 7.1), and the pH of this solution was then adjusted to a value of 8.5 by adding a 1N aqueous solution of sodium hydroxide, whilst ice-cooling. 200 mg of ethyl acetimidate hydrochloride were added to the resulting solution, and the pH of the mixture was again adjusted to a value of 8.5 by adding a 1N aqueous solution of sodium hydroxide; the mixture was then stirred for 30 minutes, whilst ice-cooling. The pH of this solution was adjusted to a value of 7 by adding dilute hydrochloric acid, and the mixture was then purified by chromatography through a column of Diaion Hp 20 AG. The fraction which was eluted with 3% v/v aqueous acetone was lyophilized to yield 102 mg of the title compound.

Nuclear Magnetic Resonance Spectrum (D$_2$O) δ ppm:
- 1.04 (3H, doublet, J=7 Hz);
- 1.10 (3H, doublet, J=6 Hz);
- 1.8–2.0 (1H, multiplet);
- 2.05 (1.5H, singlet);
- 2.09 (1.5H, singlet);
- 2.2–2.4 (1H, multiplet);
- 3.1–4.2 (9H, multiplet).

Infrared Absorption Spectrum (KBr) ν$_{max}$ cm$^{-1}$: 3400, 1755, 1680, 1635, 1590.

Ultraviolet Absorption Spectrum (H$_2$O) λ$_{max}$ nm(ε): 297.2 (8660).

EXAMPLE 10 p-Nitrobenzyl
(1R,5R,6S)-2-[(3S,5S)-5-carbamoyl-1-(p-nitrobenzyloxycarbonyl)pyrrolidin-3-ylthio]-6-[1(R)-hydroxyethyl]-1-methylcarbapen-2-em-3-carboxylate (Compound No. 117)

1 g of p-nitrobenzyl (1R,5R,6S)-6-[1(R)-hydroxyethyl]-1-methyl-2-oxocarbapenam-3-carboxylate and 898 mg of (2S,4S)-2-carbamoyl-4-mercapto-1-(p-nitrobenzyloxycarbonyl)pyrrolidine were reacted and treated as described in Example 1, to give 385 mg of the title compound.

Nuclear Magnetic Resonance Spectrum (CD$_3$COCD$_3$) δ ppm:
1.25 (6H, doublet, J = 7 Hz);
2.90 (2H, singlet);
1.7–4.7 (1H);
5.22 (2H, singlet);
5.30, 5.48 (2H, AB-quartet, J = 14 Hz);
7.60, 8.13 (2H, AB-quartet, J = 8 Hz);
7.76, 8.20 (2H, AB-quartet, J = 8 Hz).
Infrared Absorption Spectrum (KBr) ν$_{max}$ cm$^{-1}$:
3450, 3350, 1770, 1700.

EXAMPLE 11

(1R,5R,6S)-2-[(3S,5S)-5-Carbamoylpyrrolidin-3-ylthio]-6-[1(R)-hydroxyethyl]-1-methylcarbapen-2-em-3-carboxylic acid (Compound No. 75)

225 mg of p-nitrobenzyl (1R,5R,6S)-2-[(3S,5S)-5-carbamoyl-1-p-nitrobenzyloxycarbonyl)pyrrolidin-3-ylthio]-6-[1(R)-hydroxyethyl]-1-methylcarbapen-2-em-3-carboxylate (prepared as described in Example 10) were subjected to the catalytic hydrogenation procedure described in Example 2, to give 51 mg of the title compound Nuclear Magnetic Resonance Spectrum (400 MHz, D$_2$O) δ ppm:
1.02 (3H, doublet, J = 7.3 Hz);
1.10 (3H, doublet, J = 6.3 Hz);
1.62 (1H, multiplet);
2.55 (1H, multiplet);
2.85 (1H, quartet);
3.17–3.25 (2H, multiplet);
3.56–3.64 (1H, multiplet);
3.78 (1H, triplet, J = 8 Hz);
4.00–4.10 (2H, multiplet).
Infrared Absorption Spectrum (KBr) ν$_{max}$ cm$^{-1}$:
3270, 3200, 1750, 1670, 1590.

EXAMPLE 12 p-Nitrobenzyl
(5R,6S)-6-[1(R)-hydroxyethyl]-1-methoxy-2-[(3S)-1-(p-nitrobenzyloxycarbonyl)pyrrolidin-3-yl]-carbapen-2-em-3-carboxylate (Compound No. 118)

1 g of p-nitrobenzyl (5R,6S)-6-[1(R)-hydroxyethyl]-1-methoxy-2-oxocarbapenam-3-carboxylate and 820 mg of 3(S)-mercapto-1-(p-nitrobenzyloxycarbonyl)pyrrolidine were reacted and then treated as described in Example 1, to give 392 mg of the title compound.

Nuclear Magnetic Resonance Spectrum (60 MHz, CDCl$_3$) δ ppm:
1.35 (3H, doublet, J = 6 Hz);
1.8–2.4 (2H, multiplet);
3.40, 3.45 (together 3H, each singlet);
3.2–4.4 (9H, multiplet);
5.18 (2H, singlet);
5.18, 5.46 (2H, AB, J = 14 Hz);
7.46, 8.13 (4H, A$_2$B$_2$, J = 9 Hz);
7.57, 8.13 (4H, A$_2$B$_2$, J = 9 Hz).

EXAMPLE 13

(5R,6S)-6-[1(R)-Hydroxyethyl]-1-methoxy-2-[(3S)-pyrrolidin-3-ylthio]carbapen-2-em-3-carboxylic acid (Compound No. 110)

150 mg of p-nitrobenzyl (5R,6S)-6-[1(R)-hydroxyethyl]-1-methoxy-2-[(3S)-1-(p-nitrobenzyloxycarbonyl)-pyrrolidin-3-ylthio]carbapen-2-em-3-carboxylate (prepared as described in Example 12) were subjected to the catalytic hydrogenation procedure described in Example 2, to give 13 mg of the title compound.

Nuclear Magnetic Resonance Spectrum (400 MHz, D$_2$O) δ ppm:
1.04, 1.16 (together 3H, each doublet, J = 6.4 Hz);
1.85–1.95 (2H, multiplet);
2.2–2.35 (4H, multiplet);
3.13–3.5 (2H, multiplet);
3.31 (3H, singlet);
3.8–3.9 (1H, multiplet);
4.05, 4.07 (each 1H, doublet, J = 3.4 Hz);
4.08–4.18 (1H, multiplet).
Infrared Absorption Spectrum (KBr) ν$_{max}$ cm$^{-1}$:
3450, 1765, 1610.
Ultraviolet Absorption Spectrum (H$_2$O) λ$_{max}$ nm(ε):
278 (7320).

EXAMPLE 14 p-Nitrobenzyl
(5R,6S)-6-[1(R)-hydroxyethyl]-1-methoxy-2-[(3S)-1-(N-p-nitrobenzyloxycarbonylacetimidoyl)pyrrolidin-3-ylthio]carbapen-2-em-3-carboxylate (Compound No. 119)

270 mg of p-nitrobenzyl (5R,6S)-6-[1(R)-hydroxyethyl]-1-methoxy-2-oxocarbapenam-3-carboxylate and 292 mg of 3(S)-mercapto-1-(N-p-nitrobenzyloxycarbonylacetimidoyl)pyrrolidine were reacted and treated as described in Example 1, to give 670 mg of the title compound, in an impure form.

Nuclear Magnetic Resonance Spectrum (CDCl$_3$) δ ppm:
1.2–1.5 (3H, multiplet);
2.36 (3H, singlet);
2.9–3.5 (2H, multiplet);
3.0–4.4 (9H, multiplet);
3.47 (3H, singlet);
5.20, 5.46 (2H, AB, J = 13 Hz);
5.25 (2H, singlet);
7.4–8.2 (8H, A$_2$B$_2$×2).

EXAMPLE 15

(5R,6S)-2-[(3S)-1-Acetimidoylpyrrolidin-3-ylthio]-6-[1(R)-hydroxyethyl]-1-methoxycarbapen-2-em-3-carboxylic acid (Compound No. 84)

670 mg of p-nitrobenzyl (5R,6S)-6-[1(R)-hydroxyethyl]-1-methoxy-2-[(3S)-1-(N-p-nitrobenzyloxycarbonylacetimidoyl)pyrrolidin-3-ylthio]carbapen-2-em-3-carboxylate (prepared as described in Example 14) were subjected to the catalytic hydrogenation procedure described in Example 2, to give 74 mg of the title compound.

Nuclear Magnetic Resonance Spectrum (400 MHz, $D_2O$) δ ppm:
 1.13–1.18 (3H, multiplet);
 1.87–2.02 (1H, multiplet);
 2.05, 2.07, 2.09, 3.00 (together 3H, each singlet);
 3.29, 3.31 (together 3H, each singlet);
 3.4–4.15 (9H, multiplet).

Infrared Absorption Spectrum (KBr) $\nu_{max}$ cm$^{-1}$: 3330, 1765, 1675, 1590.

Ultraviolet Absorption Spectrum ($H_2O$) $\lambda_{max}$ nm(ε): 202.8 (16800), 296.6 (5490).

EXAMPLE 16 p-Nitrobenzyl (5R,6S)-1-fluoro-6-[1(R)-hydroxyethyl]-2-[(3S)-1-(N-p-nitrobenzyloxycarbonylacetimidoyl)pyrrolidin-3-ylthio]carbapen-2-em-3-carboxylate (Compound No. 120)

800 mg of p-nitrobenzyl (5R,6S)-1-fluoro-6-[1(R)-hydroxyethyl]-2-oxocarbapenam-3-carboxylate and 756 mg of 3(S)-mercapto-1-(N-p-nitrobenzyloxycarbonylacetimidoyl)pyrrolidine were reacted together and treated as described in Example 1, to give 1.2 g of the title compound.

Nuclear Magnetic Resonance Spectrum (CDCl$_3$) δ ppm:
 1.1–1.3 (3H, multiplet);
 2.25 (3H, singlet);
 2.0–2.3 (2H, multiplet);
 3.0–4.4 (9H, multiplet);
 5.15 (2H, singlet);
 5.22, 5.42 (2H, AB, J=15 Hz);
 7.3–8.3 (8H, $A_2B_2\times 2$).

EXAMPLE 17

(5R,6S)-2-[(3S)-1-Acetimidoylpyrrolidin-3-ylthio]-1-fluoro-6-[1(R)-hydroxyethyl]carbapen-2-em-3-carboxylate (Compound No. 109)

670 mg of p-nitrobenzyl (5R,6S)-1-fluoro-6-[1(R)-hydroxyethyl]-2-[(3S)-1-(N-p-nitrobenzyloxycarbonylacetimidoyl)pyrrolidin-3-ylthio]carbapen-2-em-3-carboxylate (prepared as described in Example 16) were subjected to the catalytic hydrogenation procedure described in Example 2, to give 16 mg of the title compound.

Infrared Absorption Spectrum (KBr) $\nu_{max}$ cm$^{-1}$: 3250, 1750, 1680.

EXAMPLE 18 p-Nitrobenzyl (1R,5R,6S)-2-[(3S,5S)-5-carbamoyl-1-(N-p-nitrobenzyloxycarbonylacetimidoyl)pyrrolidin-3-ylthio]-6-[1(R)-hydroxyethyl]-1-methylcarbapen-2-em-3-carboxylate (Compound No. 121)

264 mg of p-nitrobenzyl (1R,5R,6S)-6-[1(R)-hydroxyethyl]-1-methyl-2-oxocarbapenam-3-carboxylate and 311 mg of (2S,4S)-2-carbamoyl-4-mercapto-1-(N-p-nitrobenzyloxycarbonylacetimidoyl)pyrrolidine were treated in the same manner as described in Example 1, to give 839 mg of the title compound in a crude state.

This crude product was used without purification in Example 19.

EXAMPLE 19

(1R,5R,6S)-2-[(3S,5S)-1-Acetimidoyl-5-carbamoylpyrrolidin-3-ylthio]-6-[1(R)-hydroxyethyl]-1-methylcarbapen-2-em-3-carboxylic acid (Compound No. 79)

839 mg of the crude product obtained as described in Example 18 were treated in the same manner as in Example 2 to give 67 mg of the title compound.

Nuclear Magnetic Resonance Spectrum (270 MHz, $D_2O$) δ ppm:
 1.00 (3H, doublet, J=6.0 Hz);
 1.09 (3H, doublet, J=6.0 Hz);
 2.06, 2.17 (together 3H, each singlet);
 1.97–2.25 (1H, multiplet);
 2.58–2.86 (2H, multiplet);
 3.06–3.22 (1H, multiplet);
 3.24–3.40 (2H, multiplet);
 3.77–3.94 (2H, multiplet);
 3.94–3.96 (2H, multiplet).

Infrared Absorption Spectrum (KBr) $\nu_{max}$ cm$^{-1}$: 1755, 1690, 1590.

Ultraviolet Absorption Spectrum ($H_2O$) $\lambda_{max}$ nm: 298.

EXAMPLE 20 p-Nitrobenzyl (5R,6S)-6-[1(R)-hydroxyethyl]-1,1-dimethyl-2-[(3S)-1-(p-nitrobenzyloxycarbonyl)pyrrolidin-3-ylthio]carbapen-2-em-3-carboxylate (Compound No. 122)

1 g of p-nitrobenzyl (5R,6S)-6-[1(R)-hydroxyethyl]-1,1-dimethyl-2-oxocarbapenam-3-carboxylate and 840 mg of 3(S)-mercapto-1-(p-nitrobenzyloxycarbonyl)pyrrolidine were reacted and treated in the same manner as in Example 1 to give 390 mg of the title compound.

Nuclear Magnetic Resonance Spectrum (CDCl$_3$) δ ppm:
 1.08 (3H, doublet, J=5 Hz);
 1.28 (3H, singlet);
 1.33 (3H, doublet, J=4 Hz);
 1.7–2.6 (3H, multiplet);
 3.0–4.5 (8H, multiplet);
 5.15 (2H, singlet);
 5.20, 5.40 (2H, AB-quartet, J=14 Hz);
 7.47, 8.12 (2H, AB-quartet, J=9 Hz);
 7.59, 8.12 (2H, AB-quartet, J=9 Hz).

EXAMPLE 21

(5R,6S)-6-[1(R)-Hydroxyethyl]-1,1-dimethyl-2-[(3S)-pyrrolidin-3-ylthio]carbapen-2-em-3-carboxylic acid (Compound No. 123)

300 mg of the product obtained as described in Example 20 were treated in the same manner as in Example 2 to give 49 mg of the title compound.

Nuclear Magnetic Resonance Spectrum (400 MHz, $D_2O$) δ ppm:
 0.93 (3H, singlet);
 1.09 (3H, doublet, J=6.3 Hz);
 1.14 (3H, singlet);
 1.82–1.88 (1H, multiplet);
 2.03 (1H, singlet);
 2.16–2.26 (1H, multiplet);

3.13 (1H, doublet of doublets, J=12.7 & 3.9 Hz);
3.19–3.24 (1H, multiplet);
3.27 (1H, doublet of doublets, J=5.9 & 2.9 Hz);
3.32–3.39 (2H, multiplet);
3.68 (1H, doublet, J=2.4 Hz);
3.88–3.95 (1H, multiplet);
4.03–4.09 (1H, multiplet).
Infrared Absorption Spectrum (KBr) $\nu_{max}$ cm$^{-1}$: 3300, 1765, 1600.
Ultraviolet Absorption Spectrum (H$_2$O) $\lambda_{max}$ nm($\epsilon$): 279 (5750).

EXAMPLE 22

(5R,6S)-2-[(3S)-1-Acetimidoylpyrrolidin-3-ylthio]-6-[1(R)-hydroxyethyl]-1,1-dimethylcarbapen-2-em-3-carboxylic acid (Compound No. 97)

190 mg of (5R,6S)-6-[1(R)-hydroxyethyl]-1,1-dimethyl-2-[(3S)-pyrrolidin-3-ylthio]carbapen-2-em-3-carboxylic acid (prepared as described in Example 21) and 560 mg of ethyl acetimidate hydrochloride were reacted in the same manner as in Example 9 to give 120 mg of the title compound.

Nuclear Magnetic Resonance Spectrum (90 MHz, D$_2$O) $\delta$ ppm:
0.92 (3H, singlet);
1.09 (3H, doublet, J=6.0 Hz);
1.13 (3H, singlet);
2.06 (3H, singlet);
1.56–2.58 (2H, multiplet);
3.06–4.25 (8H, multiplet).
Infrared Absorption Spectrum (KBr) $\nu_{max}$ cm$^{-1}$: 3350, 3250, 1755, 1670, 1630, 1600.
Ultraviolet Absorption Spectrum (H$_2$O) $\lambda_{max}$ nm($\epsilon$): 280 (5250).

EXAMPLE 23

(1R,5R,6S) 6-[1(R)-Hydroxyethyl]-2-(2-methoxymethyl-3,4,5,6-tetrahydropyrimidin-5-ylthio)-1-methylcarbapen-2-em-3-carboxylic acid (Compound No. 90)

(a) 1.0 g of p-nitrobenzyl (1R,5R,6S)-6-[1(R)-hydroxyethyl]-1-methyl-2-oxocarbapenam-3-carboxylate and 2.0 g of 1,3-bis(p-nitrobenzyloxycarbonylamino)-2-mercaptopropane were reacted in the same manner as described in Example 1 to give 1.7 g of p-nitrobenzyl (1R,5R,6S)-1-methyl-2-[1,3-bis-(p-nitrobenzyloxycarbonylamino)propan-2-ylthio]-6-[1(R)-hydroxyethyl]-carbapen-2-em-3-carboxylate.

Nuclear Magnetic Resonance Spectrum (CDCl$_3$) $\delta$ ppm:
1.3 (6H, doublet);
2.9–3.8 (7H, multiplet);
5.1 (4H, singlet);
5.1, 5.4 (2H, AB-quartet, J=13 Hz);
7.4, 8.1 (4H, A$_2$B$_2$, J=9 Hz);
7.5, 8.1 (4H, A$_2$B$_2$, J=9 Hz).
Infrared Absorption Spectrum (KBr) $\delta_{max}$ cm$^{-1}$: 3400, 1770, 1705.

(b) 0.8 g of the product obtained as described in step (a) above was dissolved in 80 ml of tetrahydrofuran, and then 80 ml of a phosphate buffer solution (pH 6.0) and 0.45 g of platinum oxide-on-carbon were added. The mixture was stirred for 2.5 hours under a hydrogen stream. At the end of this time, the catalyst was filtered off and the solvent was distilled off at below 20° C. under reduced pressure. The residue was extracted twice with ethyl acetate. The aqueous layer was filtered to remove insoluble matter. The filtrate was ice-cooled and adjusted to a pH value of 8.5 by the addition of an aqueous solution of sodium hydroxide.

1.7 g of ethyl methoxyacetimidate hydrochloride were then added and the pH value of the mixture was again adjusted to 8.5. The mixture was stirred for 20 minutes, and then its pH value was adjusted to 7.0 by the addition of dilute hydrochloric acid. The mixture was concentrated by evaporation under reduced pressure at a temperature below 20° C. to a volume of about 70 ml. The concentrate was subjected to column chromatography through Diaion CHP-20P and eluted with 10% v/v aqueous acetone. The eluate was lyophilized to give 0.1 g of the title compound.

Infrared Absorption Spectrum (KBr) $\nu_{max}$ cm$^{-1}$: 3350, 1755, 1660, 1580.

EXAMPLE 24 p-Nitrobenzyl (1R,5R,6S)-1-methyl-2-[(3S)-1-(p-nitrobenzyloxycarbonyl)pyrrolidin-3-ylthio]-6-[1(R)-(trimethylsilyloxy)ethyl]carbapen-2-em-3-carboxylate (Compound No. 124)

980 $\mu$l of triethyl phosphite and 10 mg of hydroquinone were added to a solution of 746 mg of (3S,4R)-4-{1(R)-[(3S)-1-(p-nitrobenzyloxycarbonyl)pyrrolidin-3-ylthio]carbonylethyl}-1-(p-nitrobenzyloxyoxalyl)-3-[1(R)-(trimethylsilyloxy)ethyl]-2-azetidinone in 50 ml of toluene, and the mixture was refluxed for 1 day. The toluene was distilled off and the residue was dissolved in 80 ml of xylene. The solution was refluxed for 1 day, after which the solvent was distilled off under reduced pressure. The residue was purified by column chromatography through silica gel, eluted with a 1:2 by volume mixture of cyclohexane and ethyl acetate, to give 415 mg of the title compound.

Nuclear Magnetic Resonance Spectrum (CDCl$_3$) $\delta$ ppm:
0.10 (9H, singlet);
1.25 (6H, doublet, J=6 Hz);
1.7–2.4 (2H, multiplet);
3.1–4.4 (9H, multiplet);
5.11 (1H, doublet, J=14 Hz);
5.15 (2H, singlet);
5.24 (1H, doublet, J=14 Hz);
7.43 (2H, doublet, J=9 Hz);
7.57 (2H, doublet, J=9 Hz);
8.14 (2H, doublet, J=9 Hz).
Infrared Absorption Spectrum (CHCl$_3$) $\nu_{max}$ cm$^{-1}$: 1765, 1700.

EXAMPLE 25 p-Nitrobenzyl (1R,5R,6S)-1-methyl-2-{(3S)-1-[N-(p-nitrobenzyloxycarbonyl)acetimidoyl]pyrrolidin-3-ylthio}-6-[1(R)-(trimethylsilyloxy)ethyl]carbapen-2-em-3-carboxylate (Compound No. 125)

550 mg of (3S,4R)-4-{1(R)-[(3S)-1-(N-p-nitrobenzyloxycarbonylacetimidoyl)pyrrolidin-3-ylthio]carbonylethyl}-3-[1(R)-(trimethylsilyloxy)ethyl]-2-azetidinone were reacted and treated in the same manner as in Example 24 to give 204 mg of the title compound.

Nuclear Magnetic Resonance Spectrum (CDCl$_3$) δ ppm:
0.12 (9H, singlet);
1.26 (6H, doublet, J=7 Hz);
1.7–2.6 (2H, multiplet);
2.28 (3H, singlet);
3.0–4.4 (9H, multiplet);
5.13 (1H, doublet, J=14 Hz);
5.15 (2H, singlet);
5.27 (1H, doublet, J=14 Hz);
7.48 (2H, doublet, J=9 Hz);
7.58 (2H, doublet, J=9 Hz);
8.15 (4H, doublet, J=9 Hz).

EXAMPLE 26 p-Nitrobenzyl (1R,5R,6S)-6-[1(R)-hydroxyethyl]-1-methyl-2-[(3S)-1-(p-nitrobenzyloxycarbonyl)pyrrolidin-3-ylthio]carbapen-2-em-3-carboxylate (Compound No. 115)

279 mg of the product obtained as described in Example 24 were dissolved in 3 ml of acetonitrile, and then a solution of 65 mg of potassium fluoride in 1 ml of water was added, followed by 130 μl of acetic acid, and the whole mixture was stirred at room temperature for 1 hour. At the end of this time, ethyl acetate was added to the reaction mixture, and the whole mixture was washed with water. The solvent was removed by evaporation under reduced pressure, and then the residue was purified by short column chromatography through silica gel, eluted with a 10:1 by volume mixture of ethyl acetate and methanol, to give 237 mg of the title compound.

Nuclear Magnetic Resonance Spectrum (CDCl$_3$) δ ppm:
1.30 (3H, doublet, J=6 Hz);
1.38 (3H, doublet, J=6 Hz);
1.6–2.5 (2H, multiplet);
3.1–4.4 (10H, multiplet);
5.17 (1H, doublet, J=15 Hz);
5.20 (2H, singlet);
5.52 (1H, doublet, J=15 Hz);
7.47 (2H, doublet, J=9 Hz);
7.62 (2H, doublet, J=9 Hz);
8.20 (4H, doublet, J=9 Hz).
Infrared Absorption Spectrum (KBr) $v_{max}$ cm$^{-1}$:
3400, 1770, 1705.

We claim:
1. 2-(1-Acetimidoyl-5-carbamoylpyrrolidin-3-ylthio)-6-(1-hydroxyethyl)-1-methylcarbapen-2-em-3-carboxylic acid or a pharmaceutically acceptable salt thereof.
2. 2-(Acetimidoyl-5-carbamoylpyrrolidin-3-ylthio)-6-(1-hydroxyethyl)-1-methylcarbapen-2-em-3-carboxylic acid.

* * * * *

UNITED STATES PATENT AND TRADEMARK OFFICE
CERTIFICATE OF CORRECTION

PATENT NO. : 5,102,997
DATED : April 7, 1992
INVENTOR(S) : Yukio SUGIMURA et al

It is certified that error appears in the above-identified patent and that said Letters Patent is hereby corrected as shown below:

Title page, item (54), and column 1, line 2, in the title, delete "-YLTHIO" and insert -- -YLTHIO) --.

Title page, Section [56] References Cited, under "U.S. PATENT DOCUMENTS", delete "1,696,923  9/1927  Christensen et al....540/350" and insert --4,696,923  9/1987  Christensen et al.....540/350
  4,552,873  11/1985  Miyadera et al........260/245.2T--.

Column 14, line 18, delete "$C_1-C^3$" and insert --$C_1-C_3$--.

Signed and Sealed this

Thirtieth Day of August, 1994

Attest:

BRUCE LEHMAN

*Attesting Officer*   *Commissioner of Patents and Trademarks*